United States Patent
Maguire et al.

(10) Patent No.: US 10,537,436 B2
(45) Date of Patent: Jan. 21, 2020

(54) CURVED EXPANDABLE CAGE

(71) Applicant: DePuy Synthes Products, Inc., Raynham, MA (US)

(72) Inventors: Paul Maguire, Hope Valley, RI (US); William Frasier, New Bedford, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 294 days.

(21) Appl. No.: 15/340,448

(22) Filed: Nov. 1, 2016

(65) Prior Publication Data
US 2018/0116819 A1     May 3, 2018

(51) Int. Cl.
*A61F 2/44* (2006.01)
*A61F 2/30* (2006.01)

(52) U.S. Cl.
CPC ............ *A61F 2/4425* (2013.01); *A61F 2/442* (2013.01); *A61F 2/4455* (2013.01);
(Continued)

(58) Field of Classification Search
CPC ........ A61F 2/4425; A61F 2/443; A61F 2/442; A61F 2/4455; A61F 2/4465; A61F 2002/30411; A61F 2002/30471
See application file for complete search history.

(56) References Cited

U.S. PATENT DOCUMENTS

| | | |
|---|---|---|
| 1,802,560 A | 4/1931 | Kerwin |
| 1,924,695 A | 8/1933 | Olson |

(Continued)

FOREIGN PATENT DOCUMENTS

| | | |
|---|---|---|
| AU | 2005314079 A1 | 6/2006 |
| CN | 1177918 A | 4/1998 |

(Continued)

OTHER PUBLICATIONS

Zucherman, "A Multicenter, Prospective, Randomized Trial Evaluating the X STOP Interspinous Process Decompression System for the Treatment of Neurogenic Intermittent Claudication", SPINE, vol. 30, No. 12, pp. 1351-1358, 2005.
(Continued)

*Primary Examiner* — Matthew J Lawson
(74) *Attorney, Agent, or Firm* — BakerHostetler

(57) ABSTRACT

An expandable intervertebral implant includes a first endplate and a second endplate, a first wedge member and a second wedge member spaced from the first wedge member that couple the first and second endplates together. The first and second wedge members are configured to translate along an actuation member housed between the first and second endplates to cause the implant to expand from a first collapsed configuration into a second expanded configuration. The actuation member has a first threaded section spaced apart from a second threaded section where the first and second threaded sections are at an angle with each other. The actuation member is configured to move the first and second wedge members from the first collapsed configuration into the second expanded configuration so that the first and second endplates separate from each other to contact and engage the endplates of the adjacent vertebral bodies.

17 Claims, 18 Drawing Sheets

(52) U.S. Cl.
CPC ... *A61F 2/4465* (2013.01); *A61F 2002/30411* (2013.01); *A61F 2002/30471* (2013.01); *A61F 2002/30507* (2013.01); *A61F 2002/30556* (2013.01); *A61F 2002/30563* (2013.01); *A61F 2002/30566* (2013.01); *A61F 2002/30647* (2013.01)

(56) References Cited

U.S. PATENT DOCUMENTS

| | | |
|---|---|---|
| 2,077,804 A | 4/1937 | Morrison |
| 2,121,193 A | 6/1938 | Hanicke |
| 2,173,655 A | 9/1939 | Neracher et al. |
| 2,243,717 A | 5/1941 | Moreira |
| 2,381,050 A | 8/1945 | Hardinge |
| 2,388,056 A | 10/1945 | Hendricks |
| 2,485,531 A | 10/1949 | William et al. |
| 2,489,870 A | 11/1949 | Dzus |
| 2,570,465 A | 10/1951 | Lundholm |
| 2,677,369 A | 5/1954 | Knowles |
| 3,115,804 A | 12/1963 | Johnson |
| 3,312,139 A | 4/1967 | Di Cristina |
| 3,486,505 A | 12/1969 | Morrison |
| 3,489,143 A | 1/1970 | Halloran |
| 3,698,391 A | 10/1972 | Mahony |
| 3,760,802 A | 9/1973 | Fischer et al. |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,867,728 A | 2/1975 | Stubstad et al. |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,175,555 A | 11/1979 | Herbert |
| 4,236,512 A | 12/1980 | Aginsky |
| 4,262,665 A | 4/1981 | Roalstad et al. |
| 4,275,717 A | 6/1981 | Bolesky |
| 4,312,353 A | 1/1982 | Shahbabian |
| 4,341,206 A | 7/1982 | Perrett et al. |
| 4,349,921 A | 9/1982 | Kuntz |
| 4,350,151 A | 9/1982 | Scott |
| 4,369,790 A | 1/1983 | McCarthy |
| 4,401,112 A | 8/1983 | Rezaian |
| 4,401,433 A | 8/1983 | Luther |
| 4,409,974 A | 10/1983 | Freedland |
| 4,449,532 A | 5/1984 | Storz |
| 4,451,256 A | 5/1984 | Weikl et al. |
| 4,456,005 A | 6/1984 | Lichty |
| 4,463,753 A | 8/1984 | Gustilo |
| 4,488,543 A | 12/1984 | Tornier |
| 4,494,535 A | 1/1985 | Haig |
| 4,532,660 A | 8/1985 | Field |
| 4,537,185 A | 8/1985 | Stednitz |
| 4,545,374 A | 10/1985 | Jacobson |
| 4,573,448 A | 3/1986 | Kambin |
| 4,601,710 A | 7/1986 | Moll |
| 4,625,725 A | 12/1986 | Davison et al. |
| 4,629,450 A | 12/1986 | Suzuki et al. |
| 4,632,101 A | 12/1986 | Freedland |
| 4,640,271 A | 2/1987 | Lower |
| 4,641,640 A | 2/1987 | Griggs |
| 4,653,489 A | 3/1987 | Tronzo |
| 4,667,663 A | 5/1987 | Miyata |
| 4,686,984 A | 8/1987 | Bonnet |
| 4,688,561 A | 8/1987 | Reese |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,858,601 A | 8/1989 | Glisson |
| 4,862,891 A | 9/1989 | Smith |
| 4,863,476 A | 9/1989 | Shepperd |
| 4,871,366 A | 10/1989 | von Recum et al. |
| 4,873,976 A | 10/1989 | Schreiber |
| 4,878,915 A | 11/1989 | Brantigan |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,959,064 A | 9/1990 | Engelhardt |
| 4,963,144 A | 10/1990 | Huene |
| 4,966,587 A | 10/1990 | Baumgart |
| 4,968,317 A | 11/1990 | Toermaelae et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 5,002,557 A | 3/1991 | Hasson |
| 5,011,484 A | 4/1991 | Breard |
| 5,013,315 A | 5/1991 | Barrows |
| 5,013,316 A | 5/1991 | Goble et al. |
| 5,059,193 A | 10/1991 | Kuslich |
| 5,062,849 A | 11/1991 | Schelhas |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,114,407 A | 5/1992 | Burbank |
| 5,116,336 A | 5/1992 | Frigg |
| 5,120,171 A | 6/1992 | Lasner |
| 5,122,133 A | 6/1992 | Evans |
| 5,122,141 A | 6/1992 | Simpson et al. |
| 5,123,926 A | 6/1992 | Pisharodi |
| 5,139,486 A | 8/1992 | Moss |
| 5,158,543 A | 10/1992 | Lazarus |
| 5,167,663 A | 12/1992 | Brumfield |
| 5,167,664 A | 12/1992 | Hodorek |
| 5,169,400 A | 12/1992 | Muehling et al. |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,697 A | 1/1993 | Hasson et al. |
| 5,178,501 A | 1/1993 | Carstairs |
| 5,183,464 A | 2/1993 | Dubrul et al. |
| 5,188,118 A | 2/1993 | Terwilliger |
| 5,195,506 A | 3/1993 | Hulfish |
| 5,201,742 A | 4/1993 | Hasson |
| 5,217,462 A | 6/1993 | Asnis et al. |
| 5,217,486 A | 6/1993 | Rice et al. |
| 5,224,952 A | 7/1993 | Deniega et al. |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,246,441 A | 9/1993 | Ross et al. |
| 5,250,049 A | 10/1993 | Michael |
| 5,269,797 A | 12/1993 | Bonati et al. |
| 5,280,782 A | 1/1994 | Wilk |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,304,142 A | 4/1994 | Liebl et al. |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,324,261 A | 6/1994 | Amundson et al. |
| 5,334,184 A | 8/1994 | Bimman |

(56) References Cited

U.S. PATENT DOCUMENTS

| | | |
|---|---|---|
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,382,248 A | 1/1995 | Jacobson et al. |
| 5,387,213 A | 2/1995 | Breard et al. |
| 5,387,215 A | 2/1995 | Fisher |
| 5,390,683 A | 2/1995 | Pishardi |
| 5,395,317 A | 3/1995 | Kambin |
| 5,395,371 A | 3/1995 | Miller et al. |
| 5,401,269 A | 3/1995 | Buttner-Janz et al. |
| 5,407,430 A | 4/1995 | Peters |
| 5,415,661 A | 5/1995 | Holmes |
| 5,424,773 A | 6/1995 | Saito |
| 5,425,773 A | 6/1995 | Boyd et al. |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,790 A | 10/1995 | Dubrul |
| 5,464,427 A | 11/1995 | Curtis et al. |
| 5,470,333 A | 11/1995 | Ray |
| 5,472,426 A | 12/1995 | Bonati et al. |
| 5,474,539 A | 12/1995 | Costa et al. |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,512,037 A | 4/1996 | Russell et al. |
| 5,514,180 A | 5/1996 | Heggeness et al. |
| 5,520,690 A | 5/1996 | Errico et al. |
| 5,520,896 A | 5/1996 | De et al. |
| 5,522,899 A | 6/1996 | Michelson |
| 5,527,312 A | 6/1996 | Ray |
| 5,534,029 A | 7/1996 | Shima |
| 5,536,127 A | 7/1996 | Pennig |
| 5,540,688 A | 7/1996 | Navas |
| 5,540,693 A | 7/1996 | Fisher |
| 5,545,164 A | 8/1996 | Howland |
| 5,549,610 A | 8/1996 | Russell et al. |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,591,168 A | 1/1997 | Judet et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,639,276 A | 6/1997 | Weinstock et al. |
| 5,643,320 A | 7/1997 | Lower et al. |
| 5,645,589 A | 7/1997 | Li |
| 5,645,599 A | 7/1997 | Samani |
| 5,647,857 A | 7/1997 | Anderson et al. |
| 5,649,931 A | 7/1997 | Bryant et al. |
| 5,653,763 A | 8/1997 | Errico |
| 5,658,335 A | 8/1997 | Allen |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,676,701 A | 10/1997 | Yuan et al. |
| 5,683,465 A | 11/1997 | Shinn et al. |
| 5,693,100 A | 12/1997 | Pisharodi |
| 5,697,977 A | 12/1997 | Pisharodi |
| 5,702,391 A | 12/1997 | Lin |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,889 A | 5/1998 | Bacich et al. |
| 5,752,969 A | 5/1998 | Cunci et al. |
| 5,762,500 A | 6/1998 | Lazarof |
| 5,762,629 A | 6/1998 | Kambin |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,792,044 A | 8/1998 | Foley et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,836,948 A | 11/1998 | Zucherman et al. |
| 5,846,259 A | 12/1998 | Berthiaume |
| 5,849,004 A | 12/1998 | Bramlet |
| 5,851,216 A | 12/1998 | Allen |
| 5,860,973 A | 1/1999 | Michelson |
| 5,860,977 A | 1/1999 | Zucherman et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |

(56) References Cited

U.S. PATENT DOCUMENTS

| | | |
|---|---|---|
| 5,976,139 A | 11/1999 | Bramlet |
| 5,976,146 A | 11/1999 | Ogawa et al. |
| 5,976,186 A | 11/1999 | Bao et al. |
| 5,980,522 A | 11/1999 | Koros et al. |
| 5,984,927 A | 11/1999 | Wenstrom et al. |
| 5,984,966 A | 11/1999 | Kiema et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lehto et al. |
| 6,010,513 A | 1/2000 | Toermaelae et al. |
| 6,015,410 A | 1/2000 | Toermaelae et al. |
| 6,019,762 A | 2/2000 | Cole |
| 6,022,352 A | 2/2000 | Vandewalle |
| 6,030,162 A | 2/2000 | Huebner |
| 6,030,364 A | 2/2000 | Durgin et al. |
| 6,033,406 A | 3/2000 | Mathews |
| 6,036,701 A | 3/2000 | Rosenman |
| 6,039,761 A | 3/2000 | Li |
| 6,039,763 A | 3/2000 | Shelokov |
| 6,045,579 A | 4/2000 | Hochshuler |
| 6,048,309 A | 4/2000 | Flom et al. |
| 6,048,342 A | 4/2000 | Zucherman et al. |
| 6,053,935 A | 4/2000 | Brenneman et al. |
| 6,066,142 A | 5/2000 | Serbousek et al. |
| 6,068,630 A | 5/2000 | Zucherman et al. |
| 6,068,648 A | 5/2000 | Cole et al. |
| 6,074,390 A | 6/2000 | Zucherman et al. |
| 6,080,193 A | 6/2000 | Hochschuler et al. |
| 6,083,244 A | 7/2000 | Lubbers et al. |
| 6,090,112 A | 7/2000 | Zucherman et al. |
| 6,102,914 A | 8/2000 | Bulstra et al. |
| 6,102,950 A | 8/2000 | Vaccaro |
| 6,106,557 A | 8/2000 | Robioneck et al. |
| 6,113,637 A | 9/2000 | Gill et al. |
| 6,113,638 A | 9/2000 | Williams et al. |
| 6,117,174 A | 9/2000 | Nolan |
| 6,123,711 A | 9/2000 | Winters |
| 6,126,661 A | 10/2000 | Faccioli et al. |
| 6,126,663 A | 10/2000 | Hair |
| 6,127,597 A | 10/2000 | Beyar et al. |
| 6,129,762 A | 10/2000 | Li |
| 6,129,763 A | 10/2000 | Chauvin et al. |
| 6,146,384 A | 11/2000 | Lee et al. |
| 6,146,387 A | 11/2000 | Trott et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,161,350 A | 12/2000 | Espinosa |
| 6,162,234 A | 12/2000 | Freedland et al. |
| 6,162,236 A | 12/2000 | Osada |
| 6,168,595 B1 | 1/2001 | Durham et al. |
| 6,168,597 B1 | 1/2001 | Biedermann et al. |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,190,387 B1 | 2/2001 | Zucherman et al. |
| 6,193,757 B1 | 2/2001 | Foley et al. |
| 6,197,041 B1 | 3/2001 | Shichman et al. |
| 6,200,322 B1 | 3/2001 | Branch et al. |
| 6,206,826 B1 | 3/2001 | Mathews et al. |
| 6,206,922 B1 | 3/2001 | Zdeblick et al. |
| 6,213,957 B1 | 4/2001 | Milliman et al. |
| 6,217,509 B1 | 4/2001 | Foley et al. |
| 6,221,082 B1 | 4/2001 | Marino et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,238,397 B1 | 5/2001 | Zucherman et al. |
| 6,245,107 B1 | 6/2001 | Ferree |
| 6,248,108 B1 | 6/2001 | Toermaelae et al. |
| 6,251,111 B1 | 6/2001 | Barker et al. |
| 6,264,676 B1 | 7/2001 | Gellman et al. |
| 6,267,765 B1 | 7/2001 | Taylor et al. |
| 6,267,767 B1 | 7/2001 | Strobel et al. |
| 6,280,444 B1 | 8/2001 | Zucherman et al. |
| 6,287,313 B1 | 9/2001 | Sasso |
| 6,293,909 B1 | 9/2001 | Chu et al. |
| 6,293,952 B1 | 9/2001 | Brosens et al. |
| 6,296,647 B1 | 10/2001 | Robioneck et al. |
| 6,302,914 B1 | 10/2001 | Michelson |
| 6,306,136 B1 | 10/2001 | Baccelli |
| 6,319,254 B1 | 11/2001 | Giet et al. |
| 6,319,272 B1 | 11/2001 | Brenneman et al. |
| 6,332,882 B1 | 12/2001 | Zucherman et al. |
| 6,332,883 B1 | 12/2001 | Zucherman et al. |
| 6,332,895 B1 | 12/2001 | Suddaby |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,897 B1 | 4/2002 | Bonutti |
| 6,368,350 B1 | 4/2002 | Erickson et al. |
| 6,368,351 B1 | 4/2002 | Glenn |
| 6,371,971 B1 | 4/2002 | Tsugita et al. |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,379,363 B1 | 4/2002 | Herrington et al. |
| 6,387,130 B1 | 5/2002 | Stone |
| 6,409,766 B1 | 6/2002 | Brett |
| 6,409,767 B1 | 6/2002 | Perice et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,425,919 B1 | 7/2002 | Lambrecht |
| 6,428,541 B1 | 8/2002 | Boyd et al. |
| 6,428,556 B1 | 8/2002 | Chin |
| 6,436,140 B1 | 8/2002 | Liu et al. |
| 6,436,143 B1 | 8/2002 | Ross et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,468,277 B1 | 10/2002 | Justin et al. |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,488,710 B2 | 12/2002 | Besselink |
| 6,489,309 B1 | 12/2002 | Singh et al. |

(56) References Cited

U.S. PATENT DOCUMENTS

| | | |
|---|---|---|
| 6,491,714 B1 | 12/2002 | Bennett |
| 6,494,860 B2 | 12/2002 | Rocamora et al. |
| 6,494,893 B2 | 12/2002 | Dubrul et al. |
| 6,500,178 B2 | 12/2002 | Zucherman et al. |
| 6,506,192 B1 | 1/2003 | Gertzman et al. |
| 6,511,481 B2 | 1/2003 | Von et al. |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,527,774 B2 | 3/2003 | Lieberman |
| 6,527,803 B1 | 3/2003 | Crozet et al. |
| 6,527,804 B1 | 3/2003 | Gauchet et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,554,831 B1 | 4/2003 | Rivard et al. |
| 6,554,852 B1 | 4/2003 | Oberlander |
| 6,558,389 B2 | 5/2003 | Clark et al. |
| 6,558,424 B2 | 5/2003 | Thalgott |
| 6,562,046 B2 | 5/2003 | Sasso |
| 6,562,049 B1 | 5/2003 | Norlander et al. |
| 6,562,074 B2 | 5/2003 | Gerbec et al. |
| 6,575,979 B1 | 6/2003 | Cragg |
| 6,576,016 B1 | 6/2003 | Hochshuler et al. |
| 6,579,293 B1 | 6/2003 | Chandran |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,595,998 B2 | 7/2003 | Johnson et al. |
| 6,596,008 B1 | 7/2003 | Kambin |
| 6,599,297 B1 | 7/2003 | Carlsson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,678 B2 | 9/2003 | Nishtala et al. |
| 6,620,196 B1 | 9/2003 | Trieu |
| 6,626,944 B1 | 9/2003 | Taylor |
| 6,632,224 B2 | 10/2003 | Cachia et al. |
| 6,635,059 B2 | 10/2003 | Randall et al. |
| 6,635,362 B2 | 10/2003 | Zheng |
| 6,641,564 B1 | 11/2003 | Kraus |
| 6,641,614 B1 | 11/2003 | Wagner et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,655,962 B1 | 12/2003 | Kennard |
| 6,666,891 B2 | 12/2003 | Boehm et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,664 B1 | 1/2004 | Al-Assir |
| 6,676,665 B2 | 1/2004 | Foley et al. |
| 6,679,833 B2 | 1/2004 | Smith et al. |
| 6,682,535 B2 | 1/2004 | Hoogland |
| 6,685,706 B2 | 2/2004 | Padget et al. |
| 6,685,742 B1 | 2/2004 | Jackson |
| 6,689,152 B2 | 2/2004 | Balceta et al. |
| 6,692,499 B2 | 2/2004 | Toermaelae et al. |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,760 B2 | 4/2004 | Dorchak et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,730,126 B2 | 5/2004 | Boehm et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| 6,743,166 B2 | 6/2004 | Berci et al. |
| 6,743,255 B2 | 6/2004 | Ferree |
| 6,746,451 B2 | 6/2004 | Middleton et al. |
| 6,752,831 B2 | 6/2004 | Sybert et al. |
| 6,761,720 B1 | 7/2004 | Senegas |
| 6,770,075 B2 | 8/2004 | Howland |
| 6,773,460 B2 | 8/2004 | Jackson |
| 6,790,210 B1 | 9/2004 | Cragg et al. |
| 6,793,656 B1 | 9/2004 | Mathews |
| 6,793,678 B2 | 9/2004 | Hawkins |
| 6,796,983 B1 | 9/2004 | Zucherman et al. |
| 6,805,685 B2 | 10/2004 | Taylor |
| 6,805,695 B2 | 10/2004 | Keith et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,852,129 B2 | 2/2005 | Gerbec et al. |
| 6,855,167 B2 | 2/2005 | Shimp |
| 6,863,673 B2 | 3/2005 | Gerbec et al. |
| 6,875,215 B2 | 4/2005 | Taras et al. |
| 6,881,229 B2 | 4/2005 | Khandkar et al. |
| 6,887,243 B2 | 5/2005 | Culbert |
| 6,890,333 B2 | 5/2005 | Von et al. |
| 6,893,464 B2 | 5/2005 | Kiester |
| 6,893,466 B2 | 5/2005 | Trieu |
| 6,902,566 B2 | 6/2005 | Zucherman et al. |
| 6,908,465 B2 | 6/2005 | Von et al. |
| 6,916,323 B2 | 7/2005 | Kitchens |
| 6,921,403 B2 | 7/2005 | Cragg et al. |
| 6,923,811 B1 | 8/2005 | Carl et al. |
| 6,929,606 B2 | 8/2005 | Ritland |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 6,972,035 B2 | 12/2005 | Michelson |
| 6,997,929 B2 | 2/2006 | Manzi et al. |
| 7,004,945 B2 | 2/2006 | Boyd et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,025,746 B2 | 4/2006 | Tal |
| 7,029,473 B2 | 4/2006 | Zucherman et al. |
| 7,037,339 B2 | 5/2006 | Houfburg et al. |
| 7,041,107 B2 | 5/2006 | Pohjonen et al. |
| 7,048,736 B2 | 5/2006 | Robinson et al. |

(56) References Cited

U.S. PATENT DOCUMENTS

| | | |
|---|---|---|
| 7,060,068 B2 | 6/2006 | Tromanhauser et al. |
| 7,063,701 B2 | 6/2006 | Michelson |
| 7,063,702 B2 | 6/2006 | Michelson |
| 7,066,960 B1 | 6/2006 | Dickman |
| 7,066,961 B2 | 6/2006 | Michelson |
| 7,070,601 B2 | 7/2006 | Culbert et al. |
| 7,074,203 B1 | 7/2006 | Johanson et al. |
| 7,083,650 B2 | 8/2006 | Moskowitz et al. |
| 7,087,083 B2 | 8/2006 | Pasquet et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,118,572 B2 | 10/2006 | Bramlet et al. |
| 7,118,579 B2 | 10/2006 | Michelson |
| 7,118,598 B2 | 10/2006 | Michelson |
| 7,128,760 B2 | 10/2006 | Michelson |
| 7,153,305 B2 | 12/2006 | Johnson et al. |
| D536,096 S | 1/2007 | Hoogland et al. |
| 7,156,876 B2 | 1/2007 | Moumene et al. |
| 7,163,558 B2 | 1/2007 | Senegas et al. |
| 7,172,612 B2 | 2/2007 | Ishikawa |
| 7,179,294 B2 | 2/2007 | Eisermann et al. |
| 7,201,751 B2 | 4/2007 | Zucherman et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,238,204 B2 | 7/2007 | Le et al. |
| 7,267,683 B2 | 9/2007 | Sharkey et al. |
| 7,282,061 B2 | 10/2007 | Sharkey et al. |
| 7,306,628 B2 | 12/2007 | Zucherman et al. |
| 7,309,357 B2 | 12/2007 | Kim |
| 7,326,211 B2 | 2/2008 | Padget et al. |
| 7,326,248 B2 | 2/2008 | Michelson |
| 7,335,203 B2 | 2/2008 | Winslow et al. |
| 7,361,140 B2 | 4/2008 | Ries et al. |
| 7,371,238 B2 | 5/2008 | Soboleski et al. |
| 7,377,942 B2 | 5/2008 | Berry |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,445,637 B2 | 11/2008 | Taylor |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,488,326 B2 | 2/2009 | Elliott |
| 7,503,933 B2 | 3/2009 | Michelson |
| 7,507,241 B2 | 3/2009 | Levy et al. |
| 7,517,363 B2 | 3/2009 | Rogers |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,074 B2 | 8/2009 | Eiserman et al. |
| 7,588,574 B2 | 9/2009 | Assell et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,378 B2 | 12/2009 | Foley |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,691,120 B2 | 4/2010 | Shluzas et al. |
| 7,691,147 B2 | 4/2010 | Gutlin et al. |
| 7,699,878 B2 | 4/2010 | Pavlov et al. |
| 7,703,727 B2 | 4/2010 | Selness |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,740,633 B2 | 6/2010 | Assell et al. |
| 7,744,599 B2 | 6/2010 | Cragg |
| 7,749,270 B2 | 7/2010 | Peterman |
| 7,762,995 B2 | 7/2010 | Eversull et al. |
| 7,763,025 B2 | 7/2010 | Ainsworth |
| 7,763,055 B2 | 7/2010 | Foley |
| 7,766,930 B2 | 8/2010 | Dipoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,083 B2 | 9/2010 | Smith et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,922,729 B2 | 4/2011 | Michelson |
| 7,931,689 B2 | 4/2011 | Hochschuler et al. |
| 7,938,832 B2 | 5/2011 | Culbert et al. |
| 7,951,199 B2 | 5/2011 | Miller |
| 7,985,231 B2 | 7/2011 | Sankaran |
| 7,993,403 B2 | 8/2011 | Foley et al. |
| 7,998,176 B2 | 8/2011 | Culbert |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,105,382 B2 | 1/2012 | Olmos et al. |
| 8,109,977 B2 | 2/2012 | Culbert et al. |
| 8,118,871 B2 | 2/2012 | Gordon |
| 8,128,700 B2 | 3/2012 | Delurio et al. |
| 8,133,232 B2 | 3/2012 | Levy et al. |
| 8,177,812 B2 | 5/2012 | Sankaran |
| 8,192,495 B2 | 6/2012 | Simpson et al. |
| 8,221,501 B2 | 7/2012 | Eiserman et al. |
| 8,221,502 B2 | 7/2012 | Branch |
| 8,221,503 B2 | 7/2012 | Garcia et al. |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,440 B2 | 9/2012 | Gordon et al. |
| 8,257,442 B2 | 9/2012 | Edie et al. |
| 8,262,666 B2 | 9/2012 | Baynham et al. |

(56) References Cited

U.S. PATENT DOCUMENTS

| | | |
|---|---|---|
| 8,262,736 B2 | 9/2012 | Michelson |
| 8,267,939 B2 | 9/2012 | Cipoletti et al. |
| 8,273,128 B2 | 9/2012 | Oh et al. |
| 8,273,129 B2 | 9/2012 | Baynham et al. |
| 8,287,599 B2 | 10/2012 | McGuckin |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,366,777 B2 | 2/2013 | Matthis et al. |
| 8,382,842 B2 | 2/2013 | Greenhalgh et al. |
| 8,394,129 B2 | 3/2013 | Morgenstern et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Morgenstern et al. |
| 8,518,120 B2 | 8/2013 | Glerum et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,597,333 B2 | 12/2013 | Morgenstern et al. |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,728,160 B2 | 5/2014 | Globerman et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum |
| 8,936,641 B2 | 1/2015 | Cain |
| 8,940,052 B2 | 1/2015 | Lechmann et al. |
| 8,986,387 B1 | 3/2015 | To et al. |
| 9,005,291 B2 | 4/2015 | Loebl et al. |
| 9,039,767 B2 | 5/2015 | Raymond et al. |
| 9,039,771 B2 | 5/2015 | Glerum et al. |
| 9,060,876 B1 | 6/2015 | To et al. |
| 9,078,767 B1 | 7/2015 | McLean |
| 9,091,488 B2 | 8/2015 | Malandain |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,107,766 B1 | 8/2015 | Mclean et al. |
| 9,277,928 B2 | 3/2016 | Morgenstern |
| 9,295,562 B2 | 3/2016 | Lechmann et al. |
| 9,402,739 B2 | 8/2016 | Weiman et al. |
| 9,433,510 B2 | 9/2016 | Lechmann et al. |
| 9,463,099 B2 | 10/2016 | Levy et al. |
| 9,510,954 B2 | 12/2016 | Glerum et al. |
| 9,597,197 B2 | 3/2017 | Lechmann et al. |
| 10,307,254 B2 * | 6/2019 | Levy ................... A61F 2/442 |
| 2001/0012950 A1 | 8/2001 | Nishtala et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0049529 A1 | 12/2001 | Cachia et al. |
| 2001/0049530 A1 | 12/2001 | Culbert et al. |
| 2002/0001476 A1 | 1/2002 | Nagamine et al. |
| 2002/0010070 A1 | 1/2002 | Cales et al. |
| 2002/0032462 A1 | 3/2002 | Houser et al. |
| 2002/0055740 A1 | 5/2002 | Lieberman |
| 2002/0068976 A1 | 6/2002 | Jackson |
| 2002/0068977 A1 | 6/2002 | Jackson |
| 2002/0087152 A1 | 7/2002 | Mikus et al. |
| 2002/0091387 A1 | 7/2002 | Hoogland |
| 2002/0120335 A1 | 8/2002 | Angelucci et al. |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |
| 2002/0151976 A1 | 10/2002 | Foley et al. |
| 2002/0161444 A1 | 10/2002 | Choi |
| 2002/0165612 A1 | 11/2002 | Gerber et al. |
| 2002/0183848 A1 | 12/2002 | Ray et al. |
| 2003/0004575 A1 | 1/2003 | Erickson |
| 2003/0004576 A1 | 1/2003 | Thalgott |
| 2003/0023305 A1 | 1/2003 | McKay |
| 2003/0028250 A1 | 2/2003 | Reiley et al. |
| 2003/0040799 A1 | 2/2003 | Boyd et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0069582 A1 | 4/2003 | Culbert |
| 2003/0078667 A1 | 4/2003 | Manasas et al. |
| 2003/0083688 A1 | 5/2003 | Simonson |
| 2003/0130739 A1 | 7/2003 | Gerbec et al. |
| 2003/0135275 A1 | 7/2003 | Garcia |
| 2003/0139648 A1 | 7/2003 | Foley et al. |
| 2003/0139812 A1 | 7/2003 | Garcia |
| 2003/0139813 A1 | 7/2003 | Messerli et al. |
| 2003/0153874 A1 | 8/2003 | Tal |
| 2003/0187431 A1 | 10/2003 | Simonson |
| 2003/0204261 A1 | 10/2003 | Eiserman |
| 2003/0208122 A1 | 11/2003 | Melkent et al. |
| 2003/0208220 A1 | 11/2003 | Worley et al. |
| 2003/0220643 A1 | 11/2003 | Ferree |
| 2003/0229350 A1 | 12/2003 | Kay |
| 2003/0233102 A1 | 12/2003 | Nakamura et al. |
| 2003/0233145 A1 | 12/2003 | Landry et al. |
| 2004/0006391 A1 | 1/2004 | Reiley |
| 2004/0008949 A1 | 1/2004 | Liu et al. |
| 2004/0019359 A1 | 1/2004 | Worley et al. |
| 2004/0024463 A1 | 2/2004 | Thomas et al. |
| 2004/0030387 A1 | 2/2004 | Landry et al. |
| 2004/0049190 A1 | 3/2004 | Biedermann et al. |
| 2004/0049223 A1 | 3/2004 | Nishtala et al. |
| 2004/0054412 A1 | 3/2004 | Gerbec et al. |
| 2004/0059339 A1 | 3/2004 | Roehm et al. |
| 2004/0059350 A1 | 3/2004 | Gordon et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0093083 A1 | 5/2004 | Branch |
| 2004/0097924 A1 | 5/2004 | Lambrecht et al. |
| 2004/0097941 A1 | 5/2004 | Weiner et al. |
| 2004/0097973 A1 | 5/2004 | Loshakove et al. |
| 2004/0106925 A1 | 6/2004 | Culbert |

(56) References Cited

U.S. PATENT DOCUMENTS

| | | |
|---|---|---|
| 2004/0127906 A1 | 7/2004 | Culbert et al. |
| 2004/0127991 A1 | 7/2004 | Ferree |
| 2004/0133280 A1 | 7/2004 | Trieu |
| 2004/0143284 A1 | 7/2004 | Chin |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153065 A1 | 8/2004 | Lim |
| 2004/0153156 A1 | 8/2004 | Cohen et al. |
| 2004/0153160 A1 | 8/2004 | Carrasco |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0172133 A1 | 9/2004 | Gerber et al. |
| 2004/0186471 A1 | 9/2004 | Trieu |
| 2004/0186482 A1 | 9/2004 | Kolb et al. |
| 2004/0186570 A1 | 9/2004 | Rapp |
| 2004/0186577 A1 | 9/2004 | Ferree |
| 2004/0199162 A1 | 10/2004 | Von et al. |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0225292 A1 | 11/2004 | Sasso et al. |
| 2004/0225361 A1 | 11/2004 | Glenn et al. |
| 2004/0230309 A1 | 11/2004 | DiMauro |
| 2004/0243239 A1 | 12/2004 | Taylor |
| 2004/0249466 A1 | 12/2004 | Liu et al. |
| 2004/0254575 A1 | 12/2004 | Obenchain et al. |
| 2004/0260297 A1 | 12/2004 | Padget et al. |
| 2004/0266257 A1 | 12/2004 | Ries et al. |
| 2005/0019365 A1 | 1/2005 | Frauchiger et al. |
| 2005/0033289 A1 | 2/2005 | Warren et al. |
| 2005/0033434 A1 | 2/2005 | Berry |
| 2005/0038515 A1 | 2/2005 | Kunzler |
| 2005/0043796 A1 | 2/2005 | Grant et al. |
| 2005/0065610 A1 | 3/2005 | Pisharodi |
| 2005/0090443 A1 | 4/2005 | Michael John |
| 2005/0090833 A1 | 4/2005 | Dipoto |
| 2005/0102202 A1 | 5/2005 | Linden et al. |
| 2005/0113916 A1 | 5/2005 | Branch |
| 2005/0113917 A1 | 5/2005 | Chae et al. |
| 2005/0113927 A1 | 5/2005 | Malek |
| 2005/0118550 A1 | 6/2005 | Turri |
| 2005/0119657 A1 | 6/2005 | Goldsmith |
| 2005/0125062 A1 | 6/2005 | Biedermann et al. |
| 2005/0130929 A1 | 6/2005 | Boyd |
| 2005/0131406 A1 | 6/2005 | Reiley et al. |
| 2005/0131409 A1 | 6/2005 | Chervitz et al. |
| 2005/0131411 A1 | 6/2005 | Culbert |
| 2005/0131538 A1 | 6/2005 | Chervitz et al. |
| 2005/0137595 A1 | 6/2005 | Hoffmann et al. |
| 2005/0143734 A1 | 6/2005 | Cachia et al. |
| 2005/0149030 A1 | 7/2005 | Serhan et al. |
| 2005/0154467 A1 | 7/2005 | Peterman et al. |
| 2005/0165398 A1 | 7/2005 | Reiley |
| 2005/0165485 A1 | 7/2005 | Trieu |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177235 A1 | 8/2005 | Baynham et al. |
| 2005/0177240 A1 | 8/2005 | Blain |
| 2005/0182414 A1 | 8/2005 | Manzi et al. |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0203512 A1 | 9/2005 | Hawkins et al. |
| 2005/0216026 A1 | 9/2005 | Culbert |
| 2005/0222681 A1 | 10/2005 | Richley et al. |
| 2005/0251142 A1 | 11/2005 | Hoffmann et al. |
| 2005/0256525 A1 | 11/2005 | Culbert et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2005/0283238 A1 | 12/2005 | Reiley |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0020284 A1 | 1/2006 | Foley et al. |
| 2006/0030872 A1 | 2/2006 | Culbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041314 A1 | 2/2006 | Millard |
| 2006/0052788 A1 | 3/2006 | Thelen et al. |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki |
| 2006/0079908 A1 | 4/2006 | Lieberman |
| 2006/0084977 A1 | 4/2006 | Lieberman |
| 2006/0084988 A1 | 4/2006 | Kim |
| 2006/0085010 A1 | 4/2006 | Lieberman |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142759 A1 | 6/2006 | Arnin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0161166 A1 | 7/2006 | Johnson et al. |
| 2006/0178743 A1 | 8/2006 | Carter |
| 2006/0195103 A1 | 8/2006 | Padget et al. |
| 2006/0206207 A1 | 9/2006 | Dryer et al. |
| 2006/0217711 A1 | 9/2006 | Stevens et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235531 A1 | 10/2006 | Buettner |
| 2006/0247634 A1 | 11/2006 | Warner et al. |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0293662 A1 | 12/2006 | Boyer et al. |
| 2006/0293663 A1 | 12/2006 | Walkenhorst et al. |
| 2007/0010826 A1 | 1/2007 | Rhoda et al. |
| 2007/0010886 A1 | 1/2007 | Banick et al. |
| 2007/0016191 A1 | 1/2007 | Culbert et al. |
| 2007/0032790 A1 | 2/2007 | Aschmann et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0073399 A1 | 3/2007 | Zipnick et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0149978 A1 | 6/2007 | Shezifi et al. |
| 2007/0162005 A1 | 7/2007 | Peterson et al. |
| 2007/0162138 A1 | 7/2007 | Heinz |
| 2007/0168036 A1 | 7/2007 | Ainsworth et al. |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0191954 A1 | 8/2007 | Hansell et al. |

(56) References Cited

U.S. PATENT DOCUMENTS

| | | |
|---|---|---|
| 2007/0191959 A1 | 8/2007 | Hartmann et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0219634 A1 | 9/2007 | Greenhalgh et al. |
| 2007/0233083 A1 | 10/2007 | Abdou |
| 2007/0233089 A1 | 10/2007 | Dipoto et al. |
| 2007/0233244 A1 | 10/2007 | Lopez et al. |
| 2007/0270954 A1 | 11/2007 | Wu |
| 2007/0270968 A1 | 11/2007 | Baynham et al. |
| 2007/0276375 A1 | 11/2007 | Rapp |
| 2007/0282449 A1 | 12/2007 | De et al. |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058598 A1 | 3/2008 | Ries et al. |
| 2008/0058944 A1 | 3/2008 | Duplessis et al. |
| 2008/0065219 A1 | 3/2008 | Dye |
| 2008/0077148 A1 | 3/2008 | Ries et al. |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0108996 A1 | 5/2008 | Padget et al. |
| 2008/0132934 A1 | 6/2008 | Reilly |
| 2008/0140207 A1 | 6/2008 | Olmos |
| 2008/0147193 A1* | 6/2008 | Matthis ............... A61F 2/4425 623/17.16 |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281425 A1 | 11/2008 | Thalgott |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2009/0005870 A1 | 1/2009 | Hawkins et al. |
| 2009/0005873 A1 | 1/2009 | Slivka et al. |
| 2009/0030423 A1 | 1/2009 | Puno |
| 2009/0048631 A1* | 2/2009 | Bhatnagar .......... A61B 17/7004 606/246 |
| 2009/0054991 A1 | 2/2009 | Biyani |
| 2009/0069813 A1 | 3/2009 | Von et al. |
| 2009/0076610 A1 | 3/2009 | Afzal |
| 2009/0099568 A1 | 4/2009 | Lowry et al. |
| 2009/0105745 A1 | 4/2009 | Culbert |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski |
| 2009/0177284 A1 | 7/2009 | Rogers et al. |
| 2009/0182429 A1 | 7/2009 | Humphreys et al. |
| 2009/0192614 A1 | 7/2009 | Beger et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0275890 A1 | 11/2009 | Leibowitz et al. |
| 2009/0292361 A1 | 11/2009 | Lopez et al. |
| 2010/0016905 A1 | 1/2010 | Greenhalgh et al. |
| 2010/0040332 A1 | 2/2010 | Van et al. |
| 2010/0076492 A1 | 3/2010 | Warner et al. |
| 2010/0076559 A1 | 3/2010 | Bagga |
| 2010/0082109 A1 | 4/2010 | Greenhalgh et al. |
| 2010/0094424 A1 | 4/2010 | Woodburn et al. |
| 2010/0114147 A1 | 5/2010 | Biyani |
| 2010/0174314 A1 | 7/2010 | Mirkovic et al. |
| 2010/0179594 A1 | 7/2010 | Theofilos et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234956 A1 | 9/2010 | Attia et al. |
| 2010/0262240 A1 | 10/2010 | Chavatte et al. |
| 2010/0268231 A1 | 10/2010 | Kuslich et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0324607 A1 | 12/2010 | Davis |
| 2010/0331891 A1 | 12/2010 | Culbert et al. |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0054538 A1 | 3/2011 | Zehavi et al. |
| 2011/0071527 A1 | 3/2011 | Nelson et al. |
| 2011/0093074 A1 | 4/2011 | Glerum et al. |
| 2011/0098531 A1 | 4/2011 | To |
| 2011/0098628 A1 | 4/2011 | Yeung et al. |
| 2011/0130835 A1 | 6/2011 | Ashley et al. |
| 2011/0130838 A1 | 6/2011 | Morgenstern et al. |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0172716 A1 | 7/2011 | Glerum |
| 2011/0172774 A1 | 7/2011 | Varela |
| 2011/0238072 A1 | 9/2011 | Tyndall |
| 2011/0270261 A1 | 11/2011 | Mast et al. |
| 2011/0270401 A1 | 11/2011 | McKay |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2011/0320000 A1 | 12/2011 | O'Neil |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0197299 A1 | 8/2012 | Fabian, Jr. |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0215262 A1 | 8/2012 | Culbert et al. |
| 2012/0215316 A1* | 8/2012 | Mohr .................... A61F 2/442 623/17.16 |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0265309 A1 | 10/2012 | Glerum et al. |
| 2012/0277795 A1 | 11/2012 | Von et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2012/0323327 A1* | 12/2012 | McAfee ................ A61F 2/447 623/17.16 |

(56) References Cited

U.S. PATENT DOCUMENTS

| | | |
|---|---|---|
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2013/0325128 A1 | 12/2013 | Perloff et al. |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0094916 A1 | 4/2014 | Glerum et al. |
| 2014/0100662 A1 | 4/2014 | Patterson |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163682 A1 | 6/2014 | Lott |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0236296 A1 | 8/2014 | Wagner et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277204 A1 | 9/2014 | Sandhu |
| 2014/0277474 A1 | 9/2014 | Robinson et al. |
| 2014/0277139 A1 | 10/2014 | Vrionis et al. |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0012097 A1 | 1/2015 | Ibarra et al. |
| 2015/0012098 A1 | 1/2015 | Eastlack et al. |
| 2015/0045894 A1 | 2/2015 | Hawkins et al. |
| 2015/0066145 A1 | 3/2015 | Rogers et al. |
| 2015/0094610 A1 | 4/2015 | Morgenstern et al. |
| 2015/0094812 A1 | 4/2015 | Marden et al. |
| 2015/0094813 A1 | 4/2015 | Lechmann et al. |
| 2015/0100128 A1 | 4/2015 | Glerum et al. |
| 2015/0112398 A1 | 4/2015 | Morgenstern et al. |
| 2015/0112438 A1 | 4/2015 | McLean |
| 2015/0173916 A1 | 6/2015 | Cain et al. |
| 2015/0182347 A1 | 7/2015 | Robinson |
| 2015/0190242 A1 | 7/2015 | Blain et al. |
| 2015/0216671 A1 | 8/2015 | Cain et al. |
| 2015/0216672 A1 | 8/2015 | Cain et al. |
| 2015/0250606 A1 | 9/2015 | Mclean |
| 2015/0320571 A1 | 11/2015 | Lechmann et al. |
| 2016/0016309 A1* | 1/2016 | Swift ................ B25J 9/0075 623/24 |
| 2016/0045333 A1 | 2/2016 | Baynham |
| 2016/0081814 A1 | 3/2016 | Baynham |
| 2016/0089247 A1 | 3/2016 | Nichols et al. |
| 2016/0317317 A1 | 3/2016 | Marchek et al. |
| 2016/0106551 A1 | 4/2016 | Grimberg et al. |
| 2016/0113776 A1 | 4/2016 | Capote |
| 2016/0235455 A1 | 8/2016 | Wahl |
| 2016/0242929 A1 | 8/2016 | Voellmicke et al. |
| 2016/0256291 A1 | 9/2016 | Miller |
| 2016/0331546 A1 | 11/2016 | Lechmann et al. |
| 2016/0367265 A1 | 12/2016 | Morgenstern Lopez |
| 2017/0000622 A1 | 1/2017 | Thommen et al. |
| 2017/0100255 A1 | 4/2017 | Hleihil et al. |
| 2017/0290674 A1 | 10/2017 | Olmos et al. |

FOREIGN PATENT DOCUMENTS

| | | |
|---|---|---|
| CN | 101087566 A | 12/2007 |
| CN | 101631516 A | 1/2010 |
| CN | 101909548 A | 12/2010 |
| CN | 102164552 A | 8/2011 |
| DE | 2804936 | 8/1979 |
| DE | 3023353 A1 | 4/1981 |
| DE | 3911610 | 10/1990 |
| DE | 4012622 | 7/1997 |
| DE | 19832798 C1 | 11/1999 |
| DE | 20101793 U1 | 5/2001 |
| DE | 202008001079 | 3/2008 |
| EP | 0077159 A1 | 4/1983 |
| EP | 0260044 A1 | 3/1988 |
| EP | 0270704 A1 | 6/1988 |
| EP | 282161 | 9/1988 |
| EP | 0433717 A1 | 6/1991 |
| EP | 0525352 A1 | 2/1993 |
| EP | 0611557 A2 | 8/1994 |
| EP | 0625336 A2 | 11/1994 |
| EP | 678489 | 10/1995 |
| EP | 0853929 A2 | 7/1998 |
| EP | 1046376 A1 | 10/2000 |
| EP | 1290985 | 3/2003 |
| EP | 1374784 A1 | 1/2004 |
| EP | 1378205 A1 | 1/2004 |
| EP | 1532949 | 5/2005 |
| EP | 1541096 | 6/2005 |
| EP | 1683593 | 7/2006 |
| EP | 1698305 B1 | 8/2007 |
| EP | 1845874 A1 | 10/2007 |
| EP | 1843723 B1 | 3/2010 |
| EP | 2331023 A2 | 6/2011 |
| EP | 2368529 | 9/2011 |
| EP | 2237748 B1 | 9/2012 |
| EP | 2764851 | 8/2014 |
| FR | 2649311 A1 | 1/1991 |
| FR | 2699065 A1 | 6/1994 |
| FR | 2718635 | 10/1995 |
| FR | 2728778 A1 | 7/1996 |
| FR | 2730159 | 8/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 | 3/2006 |
| GB | 2157788 A | 10/1985 |
| GB | 2173565 A | 10/1986 |
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 10-085232 A | 4/1998 |
| JP | 11-089854 A | 4/1999 |
| JP | 2003-010197 | 1/2003 |
| JP | 2003-126266 A | 5/2003 |
| JP | 2003-526457 | 9/2003 |
| JP | 2006-516456 | 7/2006 |
| JP | 2008-126085 A | 6/2008 |
| JP | 2011-509766 A | 3/2011 |

(56) References Cited

FOREIGN PATENT DOCUMENTS

| | | |
|---|---|---|
| JP | 2011-520580 A | 7/2011 |
| JP | 4988203 B2 | 8/2012 |
| JP | 5164571 B2 | 3/2013 |
| WO | 91/09572 A1 | 7/1991 |
| WO | 93/04652 A1 | 3/1993 |
| WO | WO 1994/004100 | 3/1994 |
| WO | WO 1995/031158 | 11/1995 |
| WO | 96/28100 A1 | 9/1996 |
| WO | WO 97/00054 | 1/1997 |
| WO | 99/42062 A1 | 8/1999 |
| WO | 99/52478 A1 | 10/1999 |
| WO | WO 1999/053871 | 10/1999 |
| WO | 99/62417 A1 | 12/1999 |
| WO | WO 2000/012033 | 3/2000 |
| WO | 00/67652 | 5/2000 |
| WO | 00/76409 A1 | 12/2000 |
| WO | WO 2000/074605 | 12/2000 |
| WO | WO 01/01895 | 1/2001 |
| WO | WO 2000/53127 | 1/2001 |
| WO | WO 2001001893 | 1/2001 |
| WO | 01/12054 A2 | 2/2001 |
| WO | WO 2001/017464 | 3/2001 |
| WO | 01/68004 A2 | 9/2001 |
| WO | 01/80751 A1 | 11/2001 |
| WO | 02/43601 A2 | 6/2002 |
| WO | 03/21308 A2 | 3/2003 |
| WO | 03/43488 A2 | 5/2003 |
| WO | 2004/008949 A2 | 1/2004 |
| WO | 2004/064603 A2 | 8/2004 |
| WO | 2004/078220 A2 | 9/2004 |
| WO | 2004/078221 A2 | 9/2004 |
| WO | 2004/098453 A2 | 11/2004 |
| WO | 2005/112835 A2 | 12/2005 |
| WO | WO 2005/112834 | 12/2005 |
| WO | 2006/017507 A2 | 2/2006 |
| WO | WO 2006/047587 | 5/2006 |
| WO | 2006/063083 A1 | 6/2006 |
| WO | WO 2006/058281 | 6/2006 |
| WO | WO 2006/065419 | 6/2006 |
| WO | WO 2006/081843 | 8/2006 |
| WO | 2006/108067 A2 | 10/2006 |
| WO | WO 2007/028098 | 3/2007 |
| WO | WO 2007/048012 | 4/2007 |
| WO | 2007/119212 A2 | 10/2007 |
| WO | 2007/124130 A2 | 11/2007 |
| WO | 2008/004057 A2 | 1/2008 |
| WO | WO 2008/044057 | 4/2008 |
| WO | 2008/064842 A2 | 6/2008 |
| WO | 2008/070863 A2 | 6/2008 |
| WO | WO 2007/009107 | 8/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | 2009/147527 A2 | 12/2009 |
| WO | 2009/152919 A1 | 12/2009 |
| WO | WO 2010/068725 | 6/2010 |
| WO | 2010/136170 A1 | 12/2010 |
| WO | WO 2010/148112 | 12/2010 |
| WO | 2011/079910 A2 | 7/2011 |
| WO | WO 2011/142761 | 11/2011 |
| WO | 2011/150350 A1 | 12/2011 |
| WO | WO 2012/009152 | 1/2012 |
| WO | WO 2012/089317 | 7/2012 |
| WO | 2012/122294 A1 | 9/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/062903 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |
| WO | WO 2014/144696 | 9/2014 |
| WO | WO 2016/069796 | 5/2016 |
| WO | WO 2016/127139 | 8/2016 |

OTHER PUBLICATIONS

Vikram Talwar, "Insertion loads of the X STOP Interspinous Process Distraction System Designed to Treat Neurogenic Intermittent Claudication", Eur Spine J. (2006) 15: pp. 908-912.

Talwar "Insertion loads of the X STOP interspinous process distraction system designed to treat neurogenic intermittent claudication", Eur Spine J. (2006) 15: pp. 908-912.

Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.

ProMap TM EMG Navigation Probe. Technical Brochure Spineology Inc, Dated May 2009.

Niosi, Christina A., "Biomechanical Characterization of the three-dimentinoal kinematic behavior of the Dynesys dynamic stabilization system: an in vitro study", Eur Spine J. (2006) 15: pp. 913-922.

Morgenstern R; "Transforaminal Endoscopic Stenosis Surgery—A Comparative Study of Laser and Reamed Foraminoplasty", in European Musculoskeletal Review, Issue 1, 2009.

Medco Forum, "Percutaneous Lumbar Fixation via PERPOS System From Interventional Spine", Oct. 2007, vol. 14, No. 49.

Medco Forum, "Percutaneous Lumbar Fixation Via PERPOS PLS System Interventional Spine", Sep. 2008, vol. 15, No. 37.

Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.

King, M.D., Don, "Internal Fixation for Lumbosacral Fusion", The Journal of Bone and Joint Surgery, J. Bone Joint Surg Am., 1948; 30: 560-578.

Kambin et al., "Percutaneous Lateral Discectomy of the Lumbar Spine: A Preliminary Report", Clin. Orthop,: 1983, 174: 127-132.

Iprenburg et al., "Transforaminal Endoscopic Surgery in Lumbar Disc Herniation in an Economic Crisis—The TESSYS Method", US Musculoskeletal, 2008, p. 47-49.

Gray's Anatomy, Crown Publishers, Inc., 1977, pp. 33-54.

Fuchs, "The use of an interspinous implant in conjuction with a graded facetectomy procedure", Spine vol. 30, No. 11, pp. 1266-1272, 2005.

Chin, "Early Results of the Triage Medical Percutaneous Transfacet Pedicular BONE-LOK Compression Device for Lumbar Fusion", Accessed online Jul. 10, 2017, 10 pages.

Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.

Brochure for PERPOS PLS System Surgical Technique by Interventional Spine, 2008, 8 pages.

Alfen et al., "Developments in the area of Endoscopic Spine Surgery", European Musculoskeletal Review 2006, pp. 23-24, ThessysTM, Transforaminal Endoscopic Spine Systems, joi max Medical Solutions.

Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.

Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).

Gore, Technique of Cervical Interbody Fusion, Clinical Orthopaedics and Related Research, 1984, pp. 191-195, No. 188.

(56) References Cited

OTHER PUBLICATIONS

Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
Hoogland, T. et al., Total Lumbar Intervertebral Disc Replacement: testing of a New Articulating Space in Human Cadaver Spines—24 1 Annual ORS, Dallas TX, Feb. 21-23, 1978, 8 pages.
*Spine Solutions Brochure—Prodisc 2001*, 16 papes.
Link SB Charite Brochure—Intervertebral Prosthesis 1988, 29 pages.
U.S. Appl. No. 60/942,998, Method and Apparatus for Spinal Stabilization, filed Jun. 8, 2007.
U.S. Appl. No. 61/675,975, Expandable Implant, filed Jul. 26, 2012.
U.S. Appl. No. 60/397,588, Method and apparatus for spinal fixation, filed Jul. 19, 2002.
U.S. Appl. No. 60/794,171, Method and apparatus for spinal fixation, filed Apr. 21, 2006.
U.S. Appl. No. 60/424,055, filed Nov. 5, 2002, entitled Method and apparatus for spinal fixation.

* cited by examiner

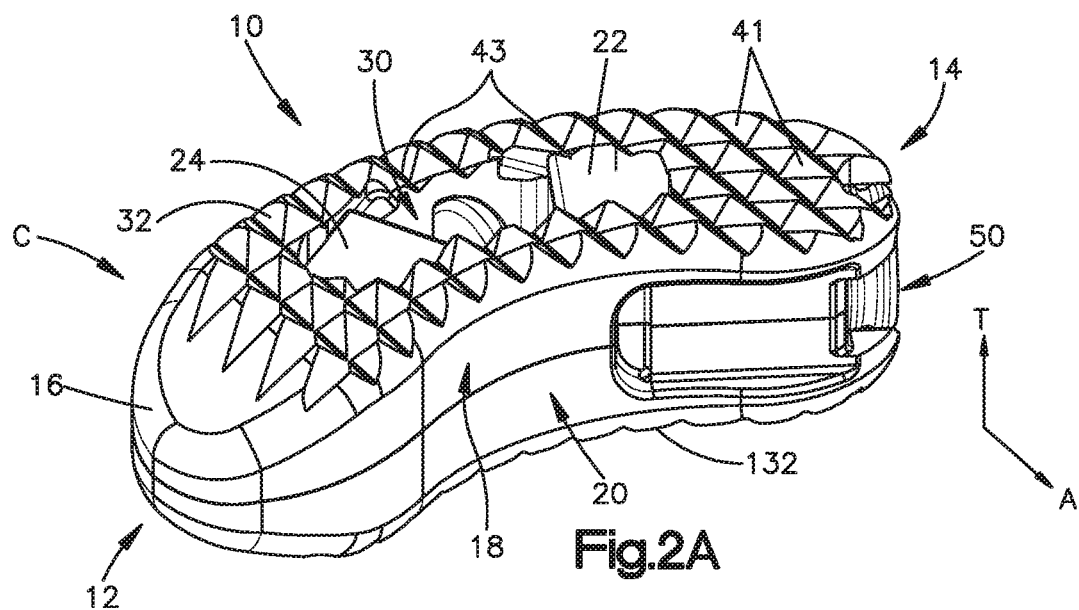
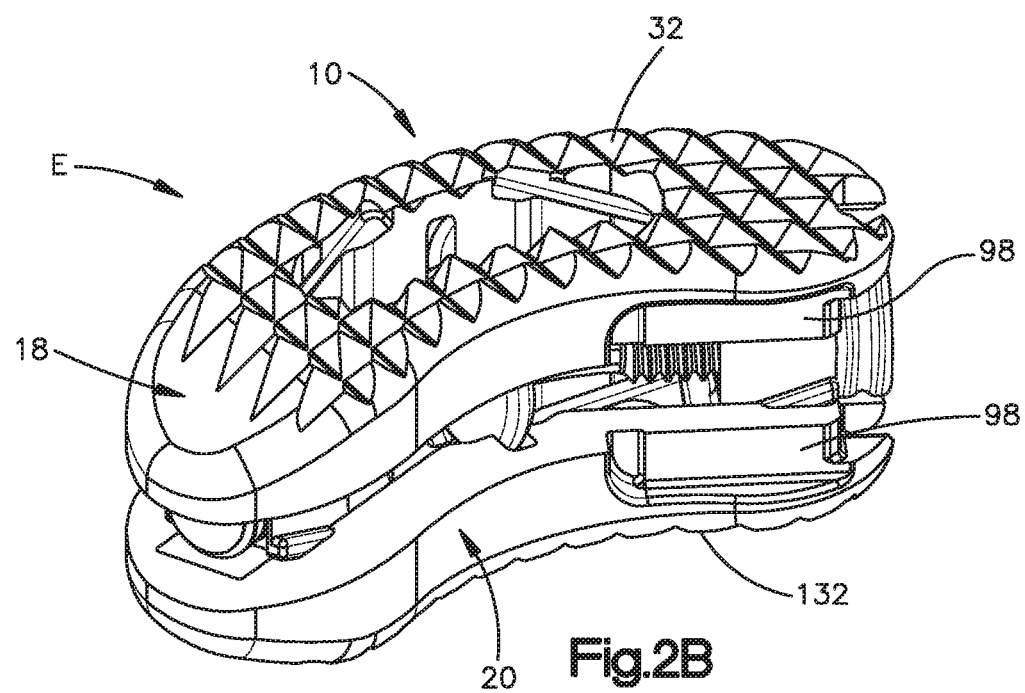

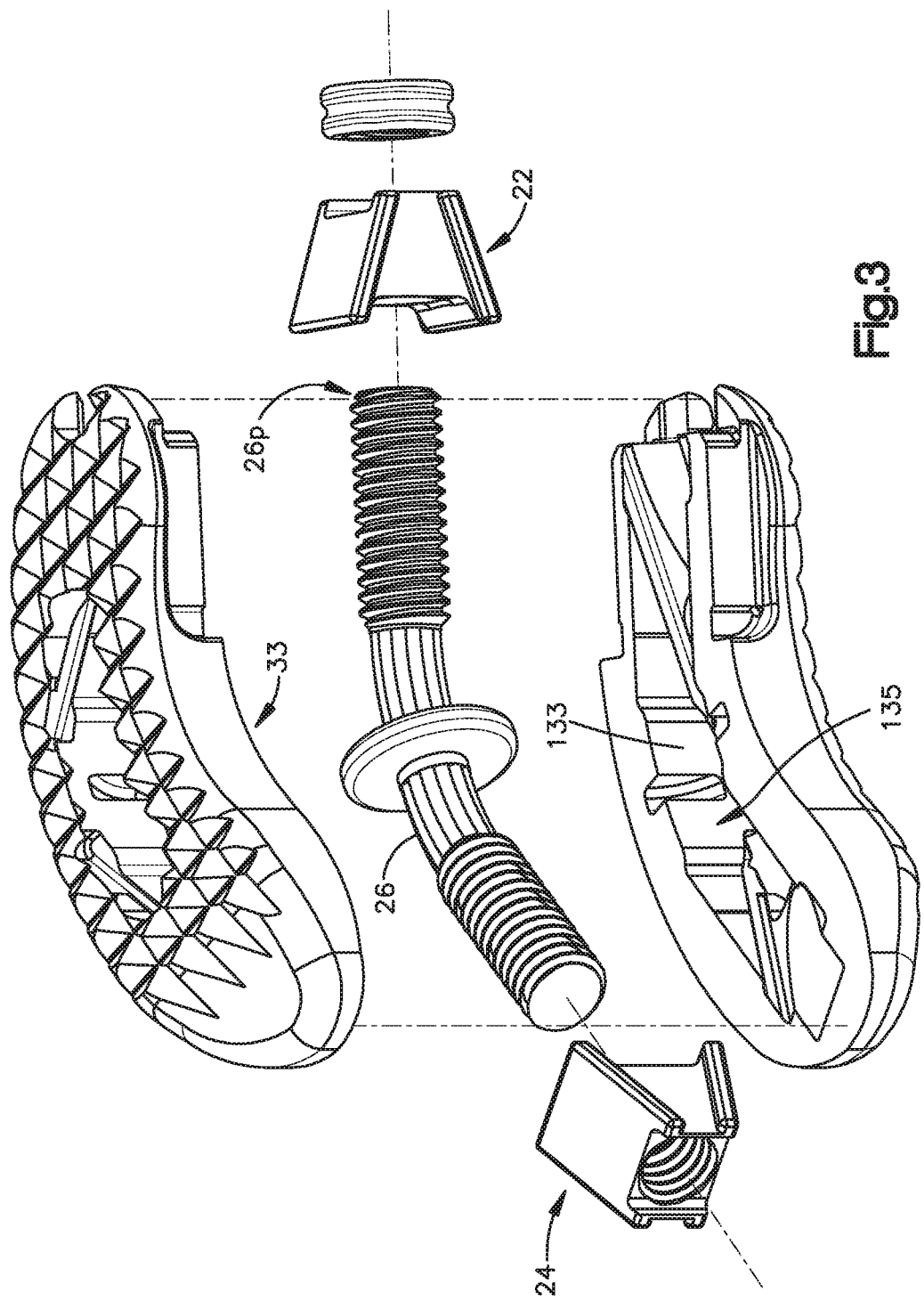

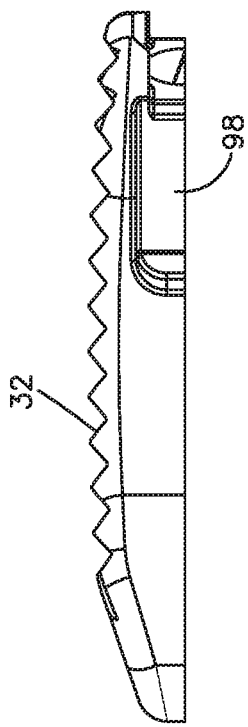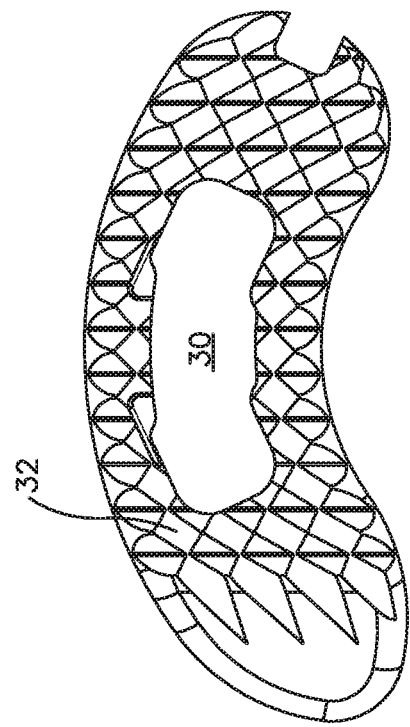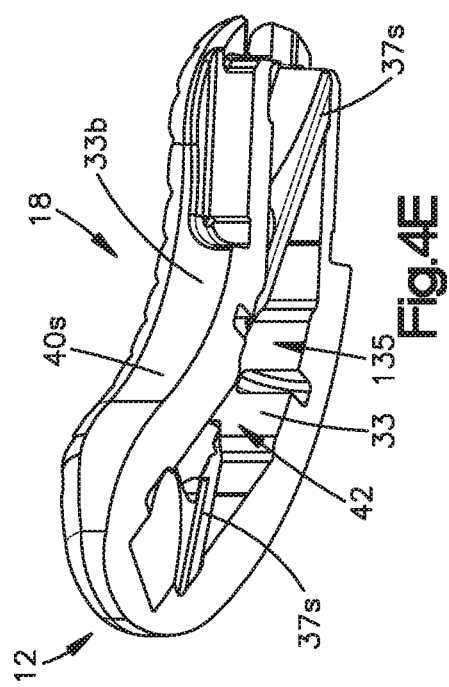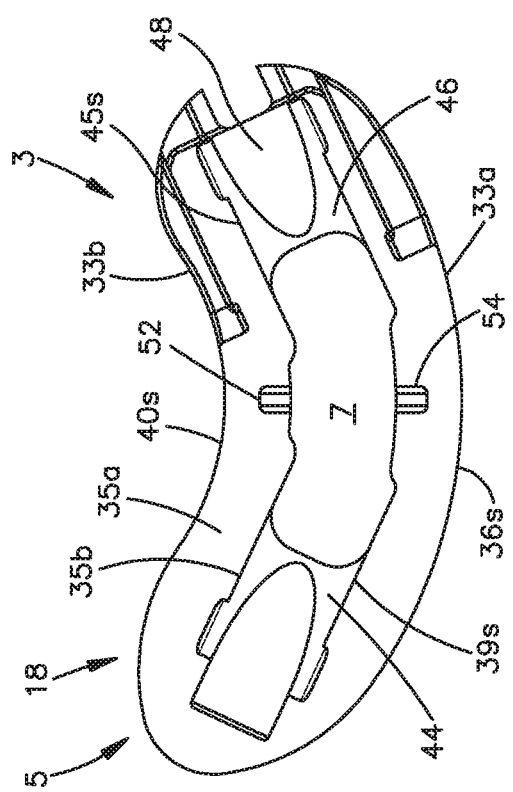

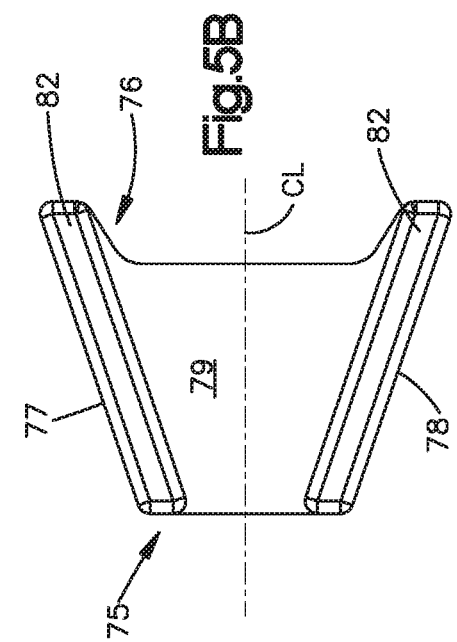
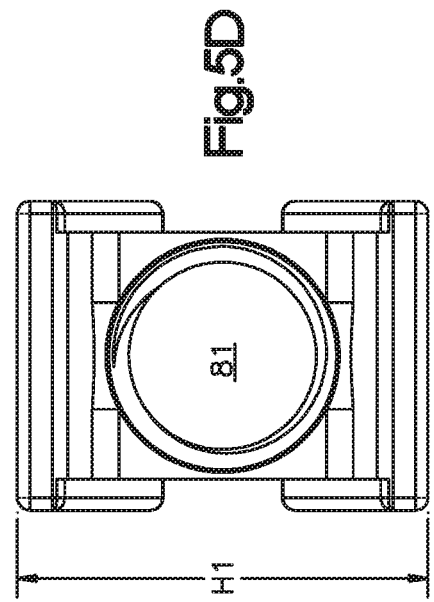
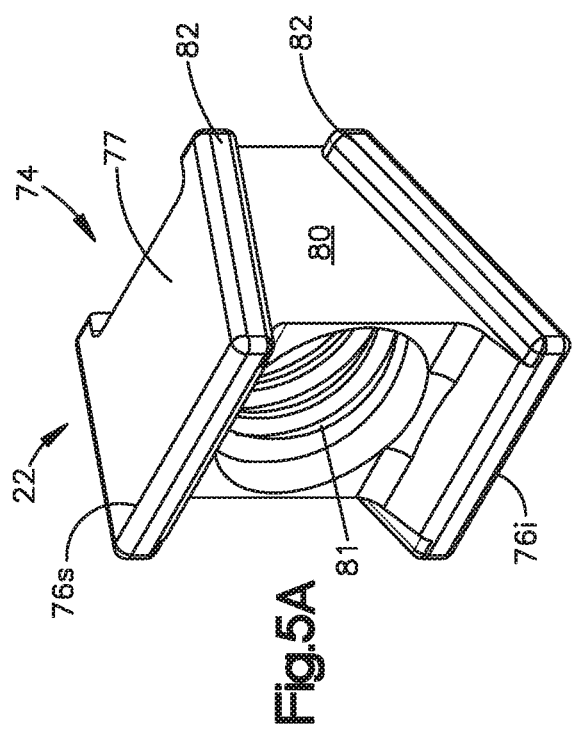
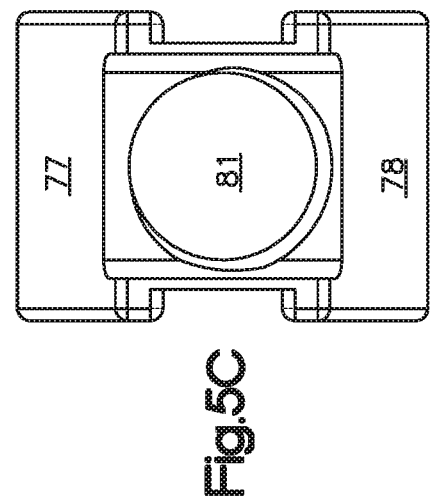

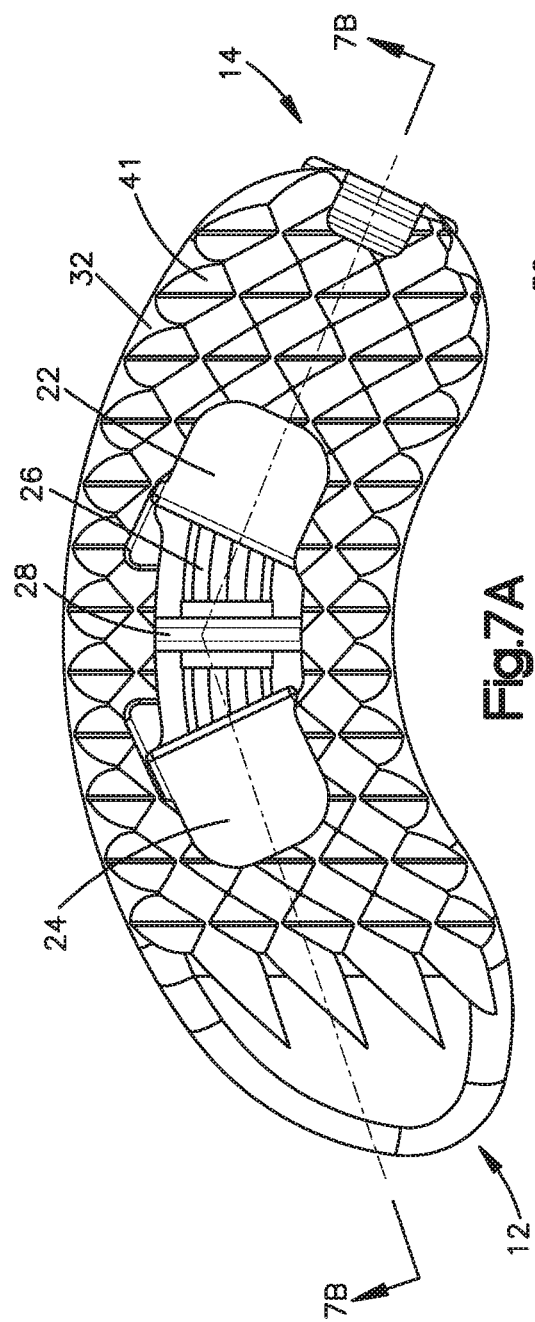
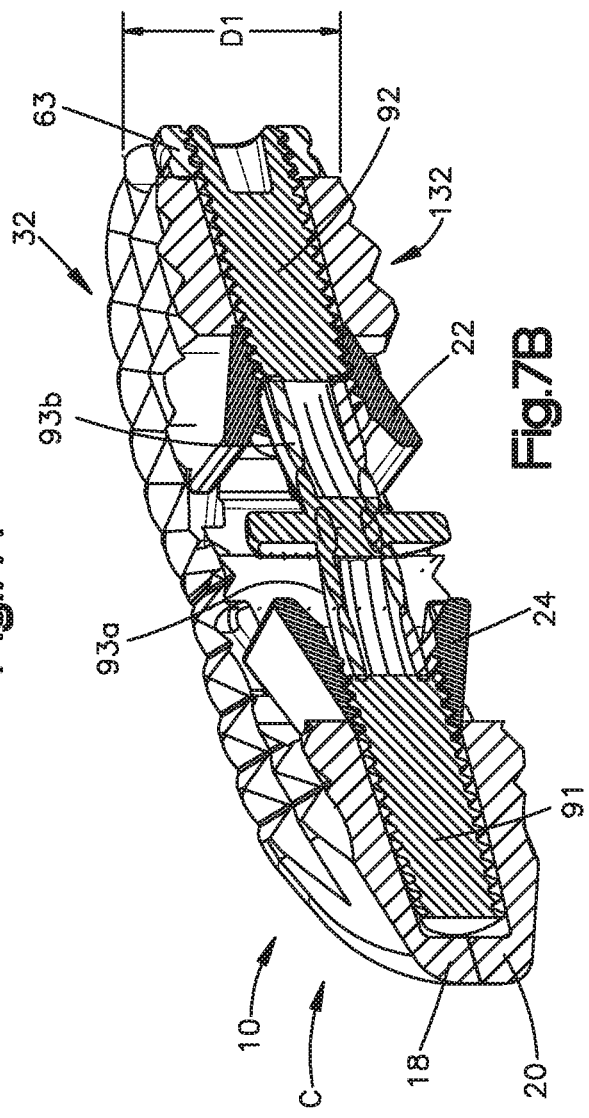

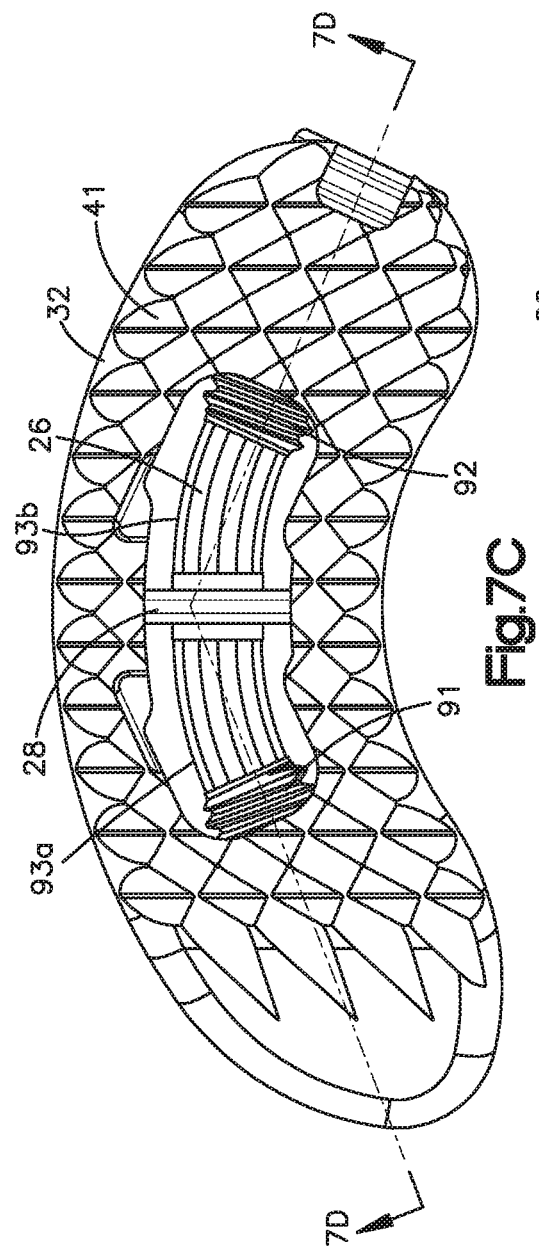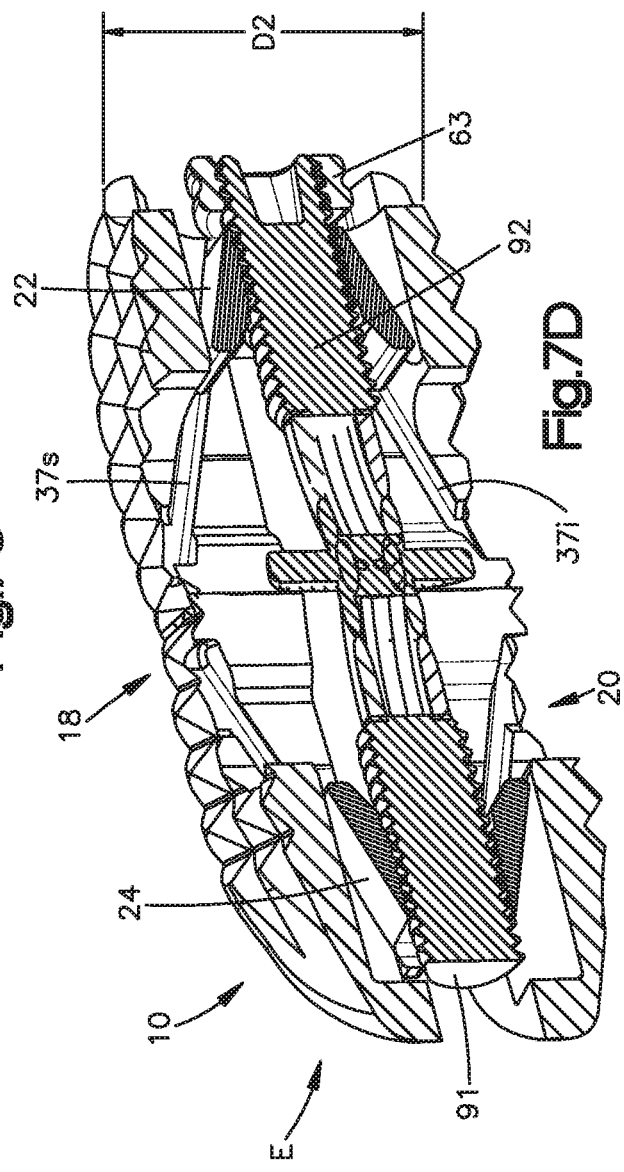

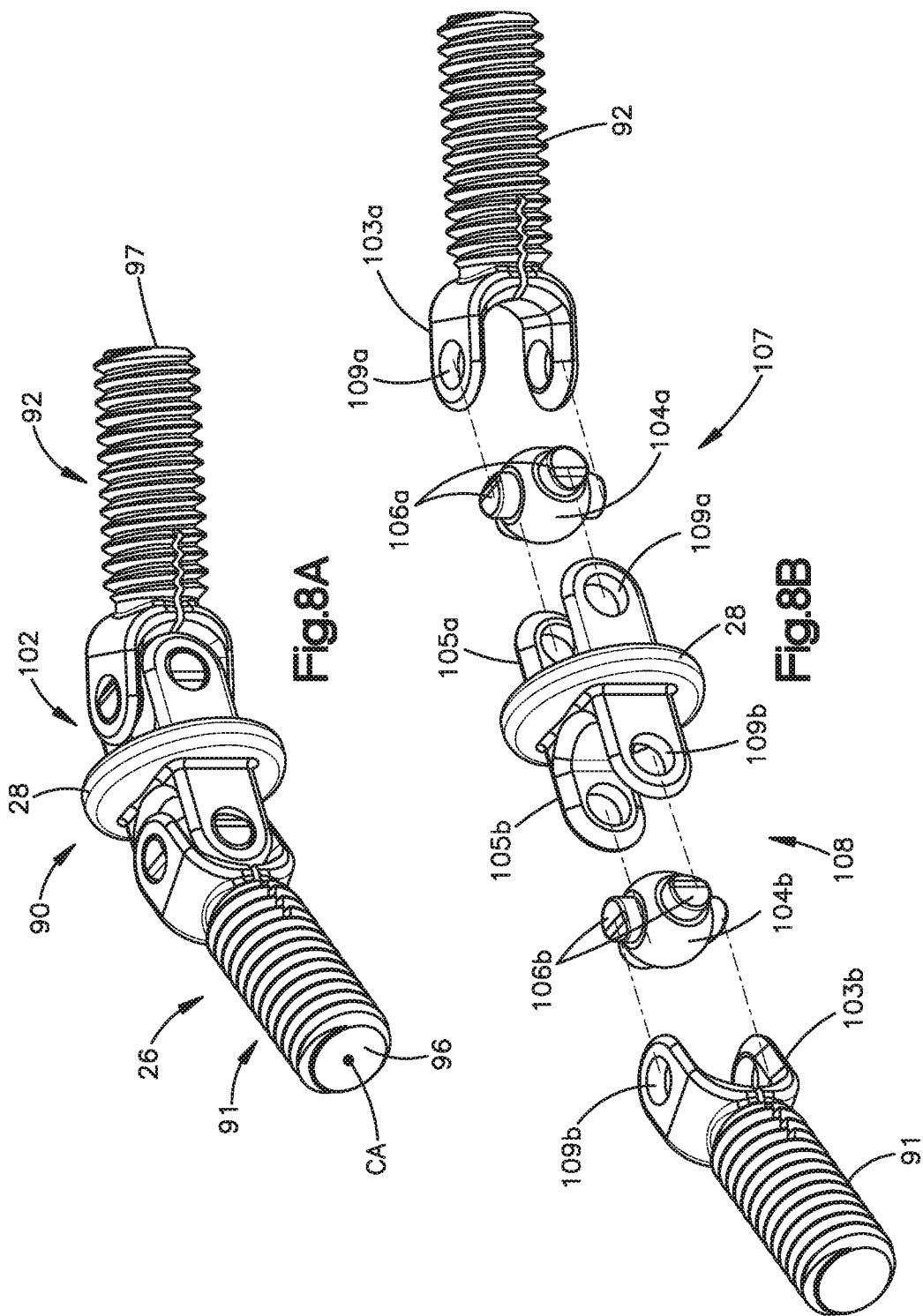

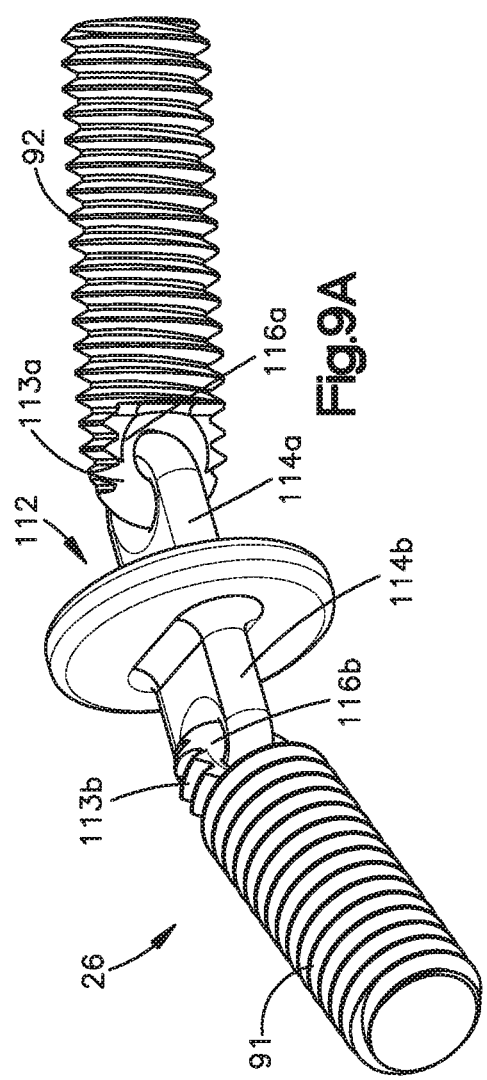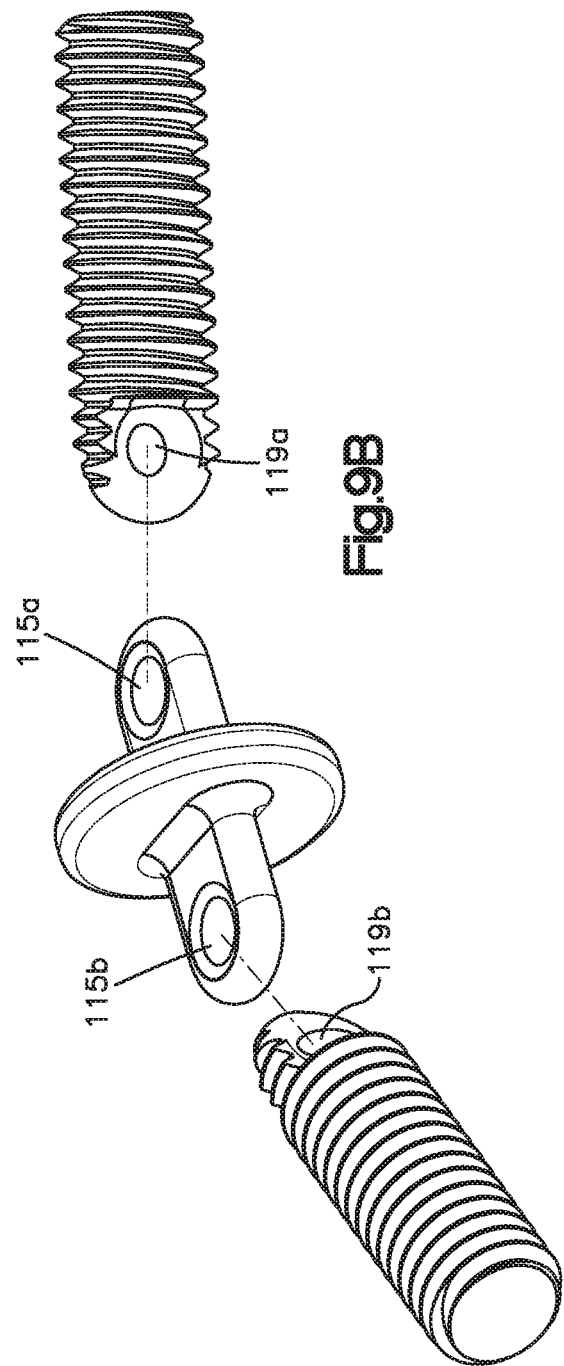

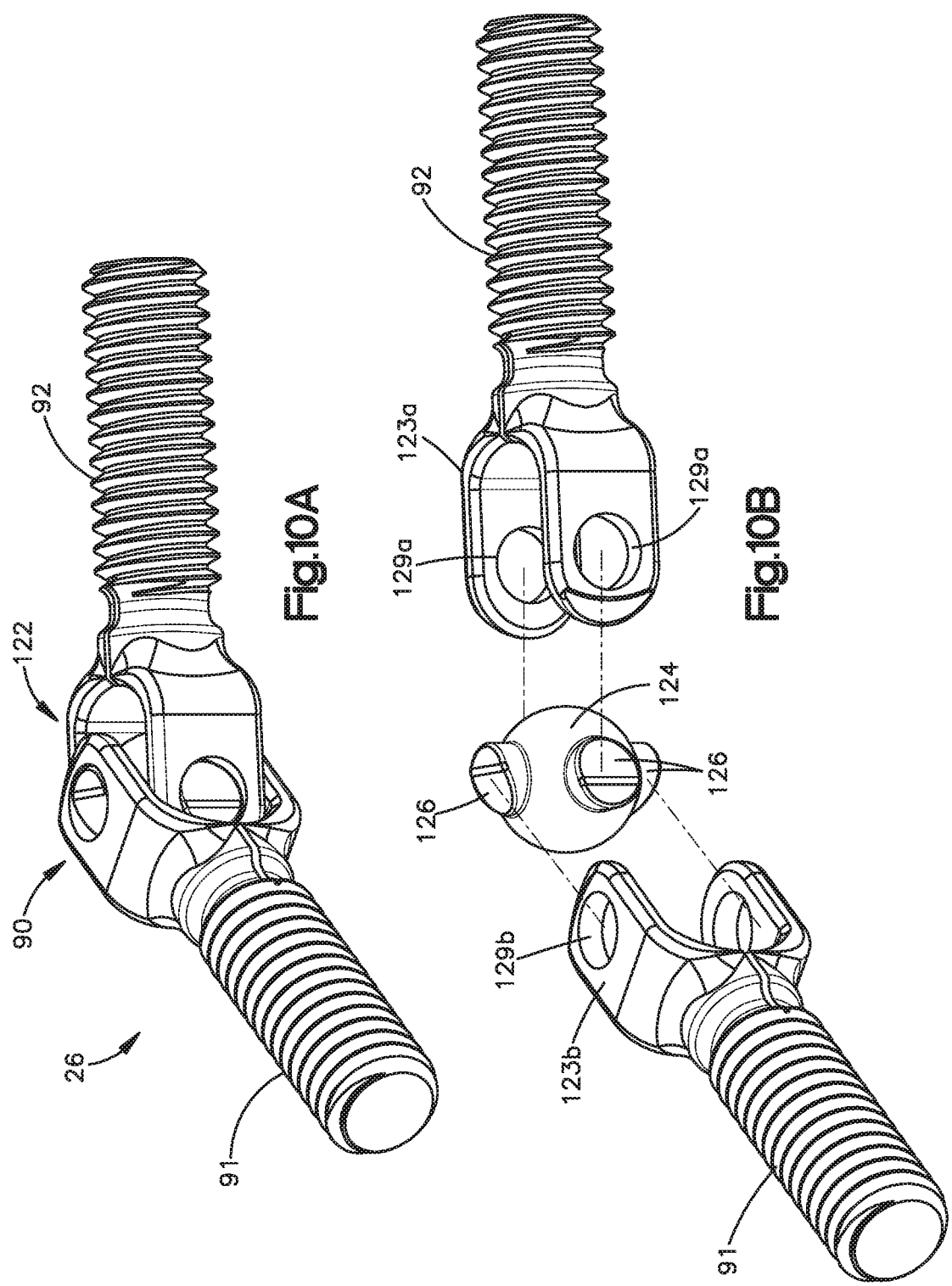

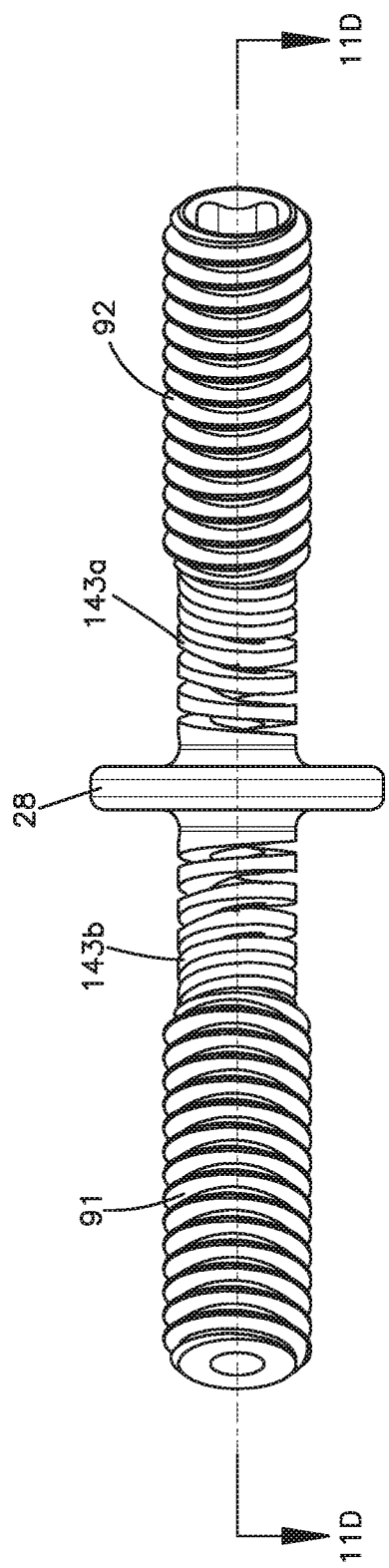
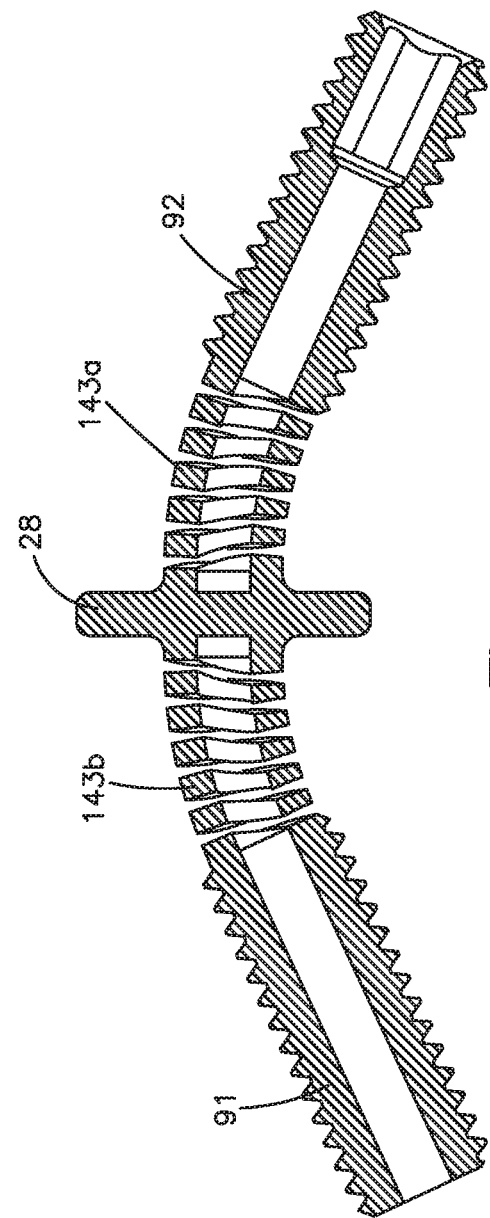

CURVED EXPANDABLE CAGE

TECHNICAL FIELD

The present invention relates to an expandable intervertebral implant, system, kit and method.

BACKGROUND

The human spine is comprised of a series of vertebral bodies separated by intervertebral discs. The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1.beta. and TNF-.alpha. as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophases) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, which may cause the nucleus pulposus to contact the spinal cord and produce pain.

One proposed method of managing these problems is to remove the problematic disc and replace it with a device that restores disc height and allows for bone growth between the adjacent vertebrae. These devices are commonly called fusion devices, or "interbody fusion devices". Current spinal fusion procedures include transforaminal lumbar interbody fusion (TLIF), posterior lumbar interbody fusion (PLIF), and extreme lateral interbody fusion (XLIF) procedures.

SUMMARY

The present invention relates to expandable intervertebral implants. The expandable intervertebral implants are preferably fusion implants used to fuse two adjacent vertebral bodies in the spine.

In a preferred embodiment, the implant is constructed with an actuation member that can be rotated to expand and contract two opposing endplates of the implant. The actuation member has a first threaded section and a second threaded section where each threaded section extends along a straight central longitudinal portion of the actuation member. The first threaded section is angularly offset from the second threaded section, the angle offset preferably between 15° and 55°. Along the actuation member between the first and second threaded section is a section that can flexibly rotate such that rotation of the first threaded section in a first rotational direction causes the second threaded section to also rotate in the first rotational direction. The threading on the first and second threaded sections is preferably opposite. Wedge members are positioned onto the first and second threaded sections and the wedge members translate along the threaded sections to enable the implant to expand from a collapsed configuration to an expanded configuration.

According to one embodiment of the present invention the expandable implant is designed for insertion into an intervertebral space between a superior vertebral body and an adjacent inferior vertebral body. The expandable implant comprises a superior endplate having a superior outer surface for contacting the superior vertebral body and an superior inner surface opposite the superior outer surface along a transverse direction. The implant also comprises an inferior endplate having an inferior outer surface for contacting the inferior vertebral body and an inferior inner surface opposite the inferior outer surface along the transverse direction. The superior endplate is movably coupled to the inferior endplate such that the superior endplate can be translated relative to the inferior endplate along the transverse direction. The implant comprises an insertion end portion and a trailing end portion opposite the insertion end portion and a first side surface and a second side surface opposite the first side surface along a lateral direction perpendicular to the transverse direction. An actuation member is housed at least partially between the inferior endplate and the superior endplate, the actuation member having a first threaded section extending along a first central longitudinal axis of the actuation member and a second threaded section extending along a second central longitudinal axis of the actuation member, wherein the first central longitudinal axis and the second central longitudinal axis form an angle between about 15° and about 75°. A first wedge member is threadedly mated with the first threaded section and a second wedge member is threadedly mated with the second threaded section. When the actuation member is rotated around the first and second central longitudinal axes the first wedge translates along the first threaded section and the second wedge translates along the second threaded section to cause the superior endplate to move apart from the inferior endplate in the transverse direction from a collapsed implant configuration to an expanded implant configuration.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 2A is a perspective view of the implant shown in FIG. 1 in a collapsed configuration;

FIG. 2B is a perspective view of the implant shown in FIG. 1 in an expanded configuration;

FIG. 3 is an exploded perspective view of the implant shown in FIG. 1;

FIG. 4E is a perspective view of the superior endplate of the implant shown in FIG. 1;

FIG. 4F is side view of the endplate of the implant shown in FIG. 4E;

FIG. 4G is a bottom plan view of the endplate of the implant shown in FIG. 4E;

FIG. 4H is a top plan view of the endplate of the implant shown in FIG. 4G;

FIG. 5A is a perspective view of a wedge member of the implant shown in FIG. 1;

FIG. 5B is a side view of the wedge member illustrated in FIG. 5A;

FIG. 5C is an end view of the wedge member illustrated in FIG. 5A;

FIG. 5D is another end view of the wedge member illustrated in FIG. 5A;

FIG. 7A is a top view of the implant of FIG. 2A illustrating the implant in the collapsed configuration;

FIG. 7B is a sectional view of the implant of FIG. 7A taken along line 7B-7B, illustrating the implant in the collapsed configuration;

FIG. 7C is a top view of the implant of FIG. 2A illustrating the implant in the expanded configuration;

FIG. 7D is a sectional view of the implant of FIG. 7C taken along line 7D-7D, illustrating the implant in the expanded configuration;

FIG. 8A is a perspective view of another embodiment for the actuation member of the implant shown in FIG. 1;

FIG. 8B is an exploded view of the actuation member shown in FIG. 8A;

FIG. 9A is a perspective view of another embodiment for the actuation member of the implant shown in FIG. 1;

FIG. 9B is an exploded view of the actuation member shown in FIG. 9A;

FIG. 10A is a perspective view of another embodiment for the actuation member of the implant shown in FIG. 1;

FIG. 10B is an exploded view of the actuation member shown in FIG. 10A;

FIG. 11C is a side view of the actuation member shown in FIG. 11A;

FIG. 11D is a sectional view of the actuation member shown in FIG. 11A;

DETAILED DESCRIPTION OF ILLUSTRATIVE EMBODIMENTS

Figure 1:
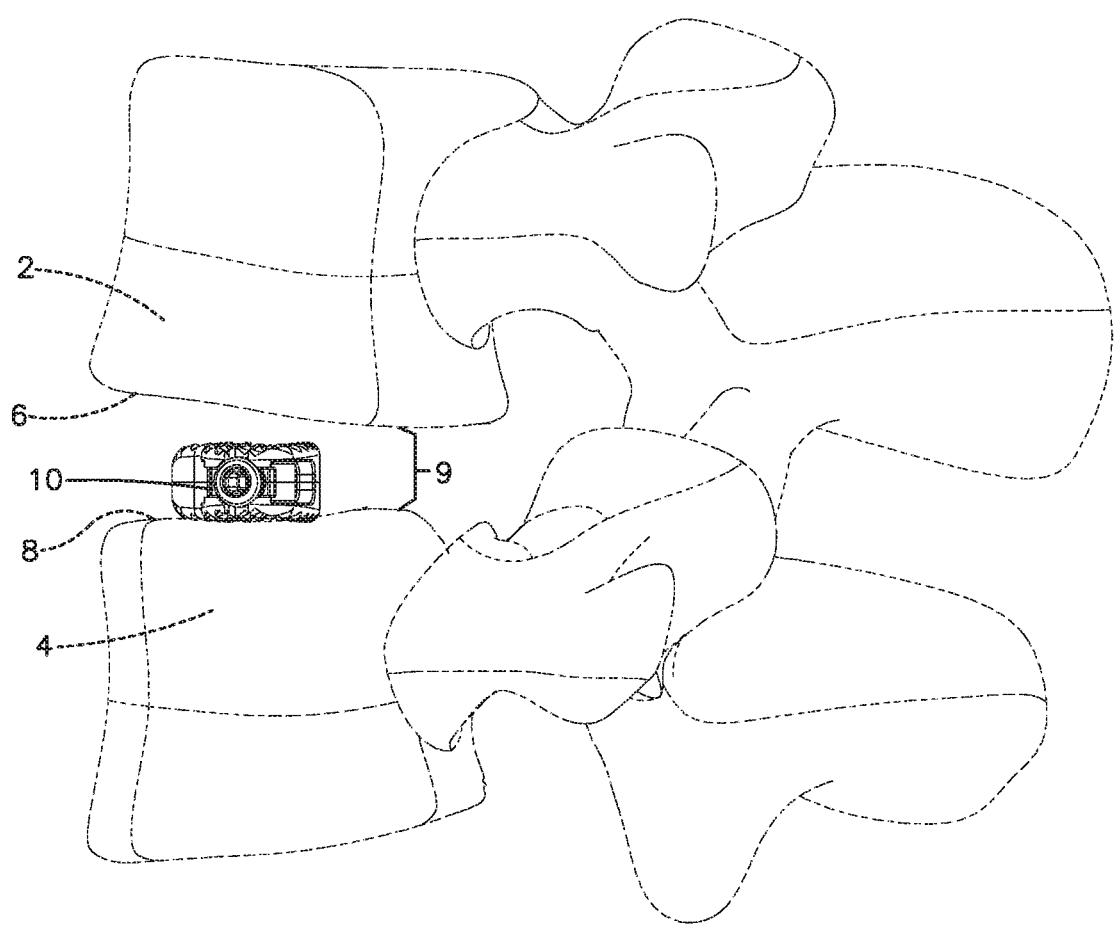
FIG. 1 illustrates an implant positioned between vertebral bodies, according to an embodiment of the present disclosure.

Referring to FIG. 1, a superior vertebral body 2 and an adjacent inferior vertebral body 4 defines an intervertebral space 9 extending between the vertebral bodies 2 and 4. The superior vertebral body 2 defines superior vertebral surface 6, and the adjacent inferior vertebral body 4 defines an inferior vertebral surface 8 (the vertebral surfaces are usually the vertebral endplates that are surgically prepared for accepting the implant). The vertebral bodies 2 and 4 are commonly anatomically adjacent, but may be the remaining vertebral bodies after an intermediate vertebral body has been removed from a location between the vertebral bodies 2 and 4. The intervertebral space 9 in FIG. 1 is illustrated after a discectomy, whereby the disc material has been removed or at least partially removed to prepare the intervertebral space 9 to receive an intervertebral implant or implant 10, as shown in FIGS. 2A-2B (the implant may also be referred to as a "spacer" or "fusion spacer" in the technical community). The inserted and expanded implant 10 is designed to achieve an appropriate height restoration for the intervertebral space 9. The intervertebral space 9 can be disposed anywhere along the spine as desired, including at the lumbar, thoracic, and cervical regions of the spine.

Referring to FIGS. 2A-2B, an embodiment of the present invention is depicted as a TLIF implant 10. The expandable intervertebral implant or implant 10 defines an implant body 13 that defines a distal or insertion end 12 and a proximal or trailing end 14 that is spaced from and opposite the insertion end 12. The implant 10 is designed and configured to be inserted into an intervertebral space in a direction from the trailing end 14 toward the insertion end 12, also referred to herein as an insertion direction. The insertion direction for a TLIF implant is generally not a straight line, but rather a curved path that may be oriented along or approximately along an implant axis that is along the center-width line of the implant 10. The trailing end 14 is configured to couple with one or more insertion instruments, which are configured to support and carry the implant 10 into the intervertebral space 9, and/or actuate the implant 10 from a collapsed configuration C shown in FIG. 2A into an expanded configuration E shown in FIG. 2B.

The implant 10 has a superior endplate or shell 18 and an inferior endplate or shell 20 that are held together and that can expand and contract relative to each other in the transverse direction T to change the height of the implant 10 within the intervertebral space 9. The superior endplate or shell 18 has a superior or outer/upper bone-contacting surface 32 and the inferior endplate or shell 20 has an inferior or outer/lower or second bone contacting surface 132 spaced from the superior bone-contacting surface 32 along the transverse direction T. The superior and inferior bone contacting surfaces 32 and 132 are configured to engage the superior and inferior vertebral bodies 2 and 4, respectively, at the respective vertebral surfaces 6, 8. Each of the superior and inferior bone contacting surfaces 32 and 132 can be convex or partially convex, for instance, one portion of the surface is convex while another portion can be planar; these surfaces can be convex along the length of the implant 10 and also convex along the width in the lateral direction A. The bone contacting surfaces 32 and 132 can also define a texture 41, such as spikes, ridges, pyramid-shapes, cones, barbs, indentations, or knurls, which are configured to engage the superior and inferior vertebral surfaces 6 and 8, respectively, when the implant 10 is inserted into the intervertebral space 9. The bone contacting surfaces 32 and 132 may be partially textured. For instance, the bone contacting surfaces 32 and 132 can include specific patterns of textured and non-textured portions. For a TLIF implant 10 as depicted, the texture 41 can be in the form of parallel, curved ridges 43 that are the peaks of the pyramid-shaped textures depicted in FIG. 2A-B, and that are curved in the insertion path direction.

As used herein, the term "proximal" and derivatives thereof refer to a direction from the distal or insertion end 12 toward the proximal end 14. As used herein, the term "distal" and derivatives thereof refer to a direction from the proximal end 14 toward the insertion end 12. As used herein, the term "superior" and derivatives thereof refer to a direction from the inferior bone contact surface 132 toward the superior bone-contacting surface 32. As used herein, the term "inferior" and derivatives thereof refer to a direction from the superior bone-contacting surface 32 toward the inferior bone contacting surface 132.

Continuing with FIGS. 2-3, the implant 10 includes a pair of wedge members coupled to an actuation member 26. The pair of wedge members includes a first wedge member 22 and a second wedge member 24 that in the preferred design function to couple the superior endplate 18 to the inferior endplate 20. The first and second wedge members 22 and 24 can translate along the actuation member 26 so as to move the superior endplate 18 relative to the inferior endplate 20 along the transverse direction T to alter the height of the implant 10; that is, as explained below, the actuation member can be rotated to move the wedge members 22, 24 along the actuation member 26 to raise and to lower the height of the implant 10 (the transverse distance between the superior and inferior bone contacting surfaces 32, 132). In this embodiment, the actuation member 26 has a relatively narrow flange 28 extending from the actuation member 26 along the transverse direction T toward the superior endplate 18 and the inferior endplate 20. In a preferred design, the superior endplate 18 has a superior inner surface 33 and the inferior endplate 20 has an inferior inner surface 133 that in conjunction define a channel 135. The implant 10 is configured such that when the implant 10 is in the collapsed configuration C shown in FIG. 2A, a substantial majority of the actuation member 26, at least a portion of first wedge member 22 and at least a portion of the second wedge member 24 are disposed within the channel 135; that is, preferably, only the proximal end portion 26p of the actuation member 26 is outside the channel 135 and the back portions of the wedge members 22, 24 are outside the channel 135 in the collapsed configuration C. The implant endplates and/or wedge members can be formed of polyether ether ketone (PEEK) or any other suitable biocompatible polymeric material, or a metal alloy. The actuation member 26 can formed from a biocompatible polymeric material or metallic alloy, such as titanium or steel. It should be appreciated that the any suitable material can be used to form the implant components as described herein. For instance, an entirety of the implant can be made from a titanium alloy. For instance, an entirety of the implant can be made from a titanium-aluminium-niobium (TAN) alloy.

Figure 4A:
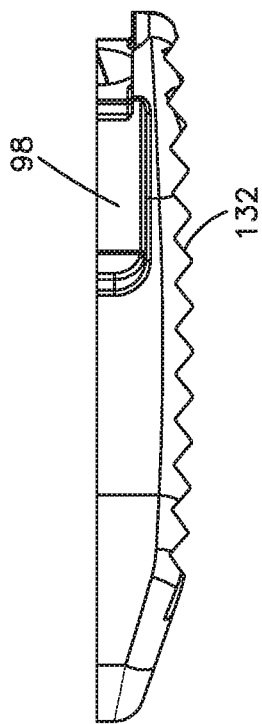
FIG. 4A is a perspective view of the inferior endplate of the implant shown in FIG. 1.
Figure 4B:
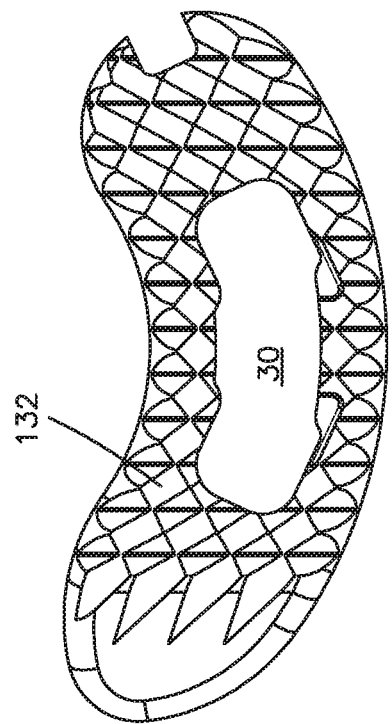
FIG. 4B is side view of the endplate of the implant shown in FIG. 4A.
Figure 4C:
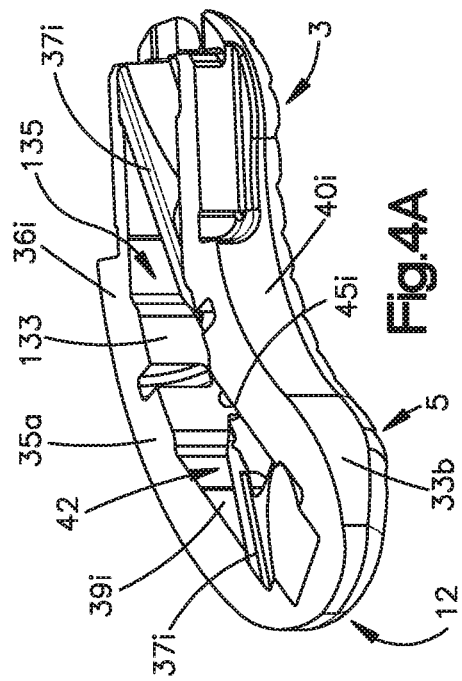
FIG. 4C is a top plan view of the endplate of the implant shown in FIG. 4A.
Figure 4D:
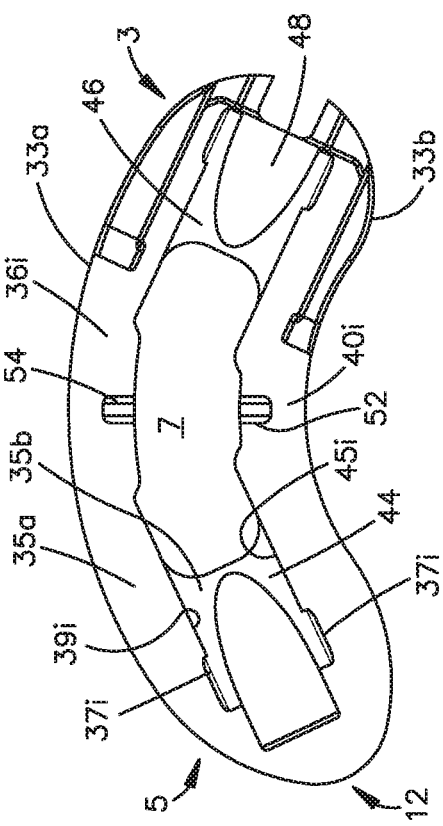
FIG. 4D is a bottom plan view of the endplate of the implant shown in FIG. 4C.
Figure 6A:
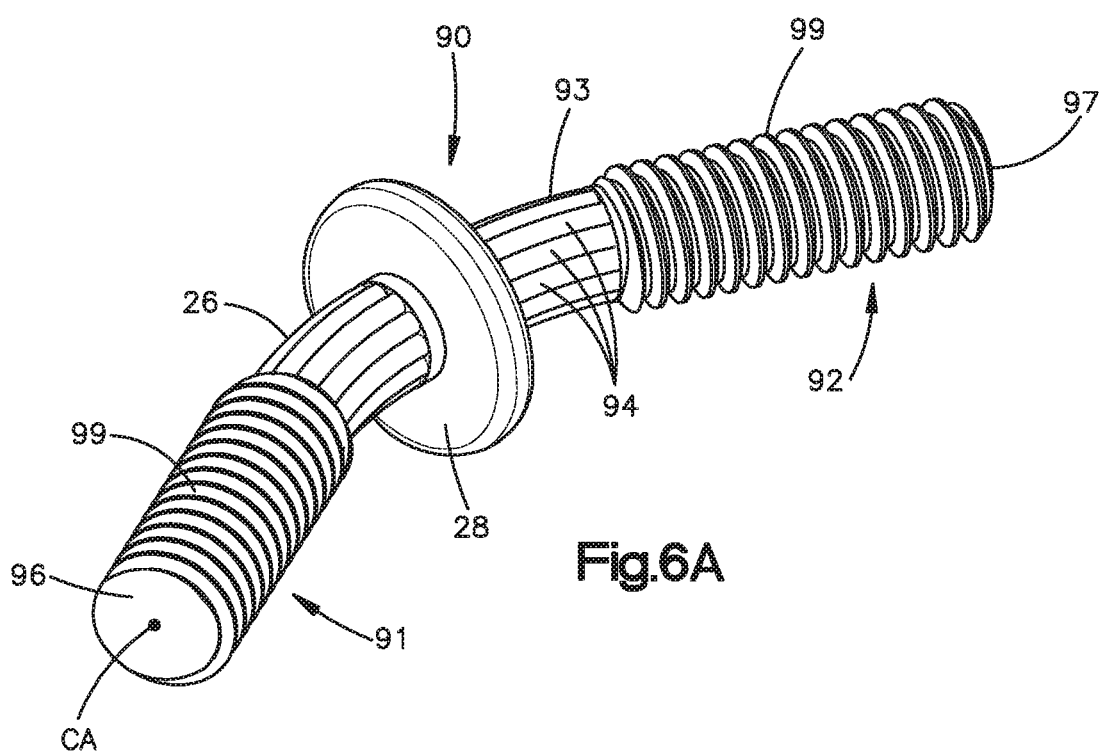
FIG. 6A is a perspective view of the actuation member of the implant shown in FIG. 1.
Figure 6B:
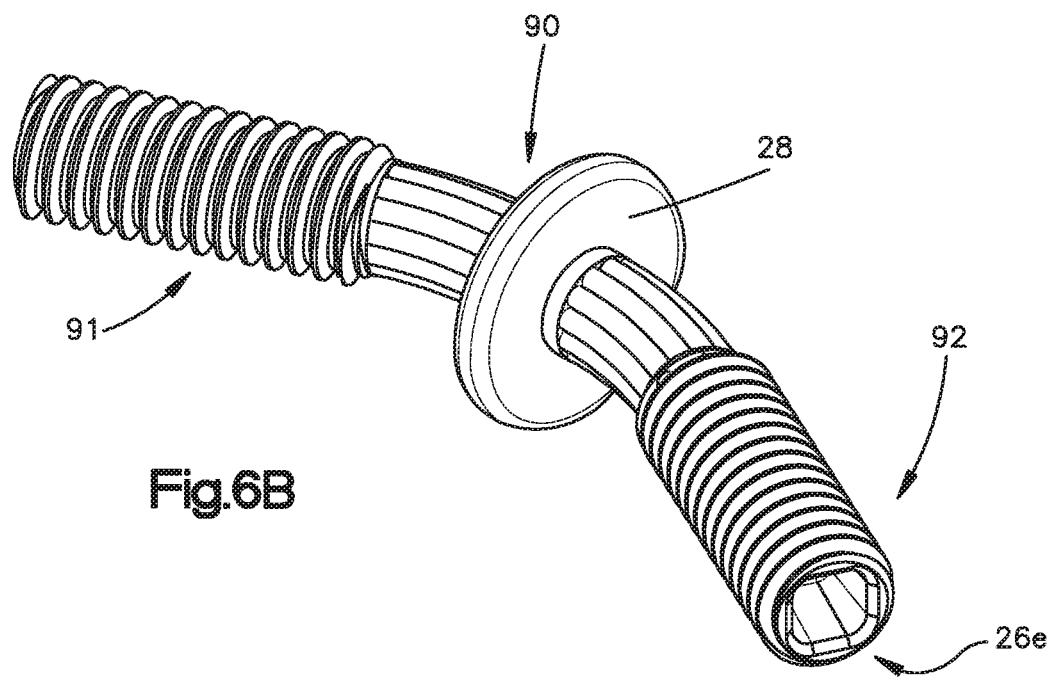
FIG. 6B is a perspective view of the actuation member of the implant shown in FIG. 1.
Figure 6C:
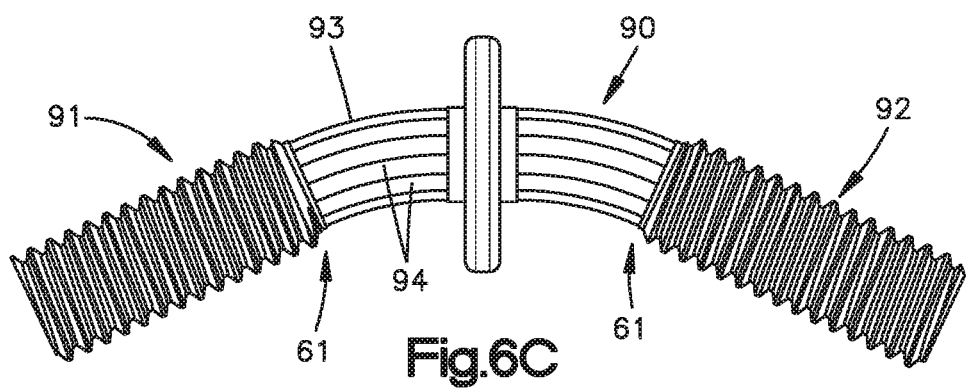
FIG. 6C is a top view of the actuation member of the implant shown in FIG. 1.
Figure 6D:
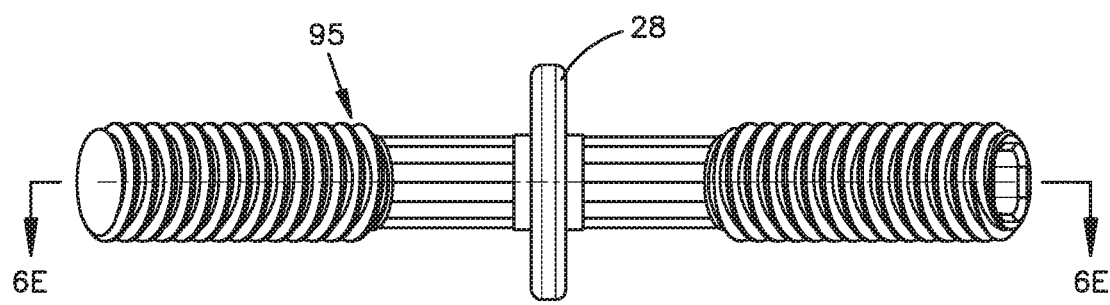
FIG. 6D is a side view of the actuation member of the implant shown in FIG. 1.
Figure 6E:
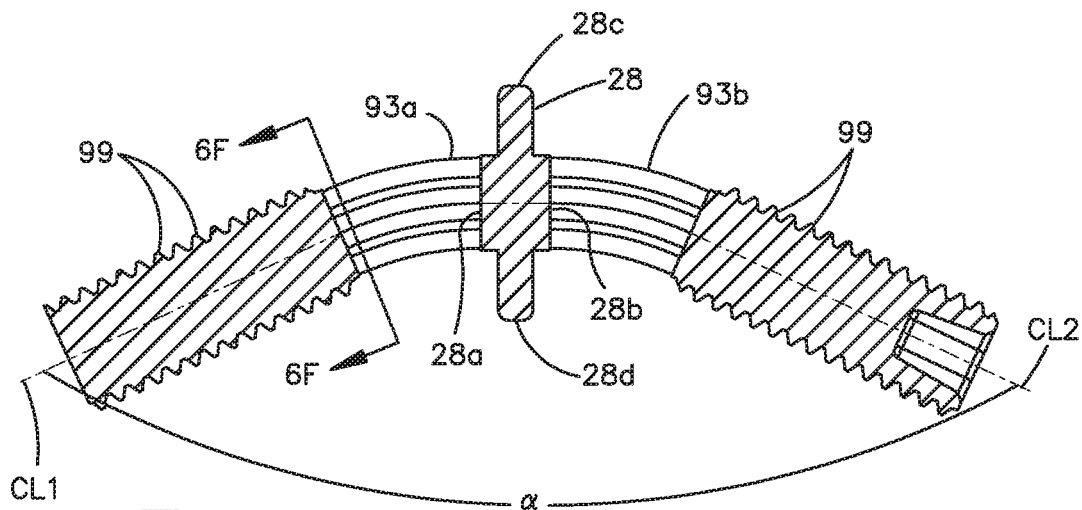
FIG. 6E is a sectional view of the actuation member of the implant shown in FIG. 6D.
Figure 6F:
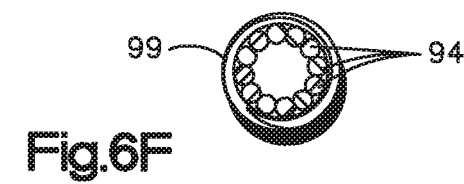
FIG. 6F is a sectional view of the actuation member of the implant shown in FIG. 6E.
Figure 8C:
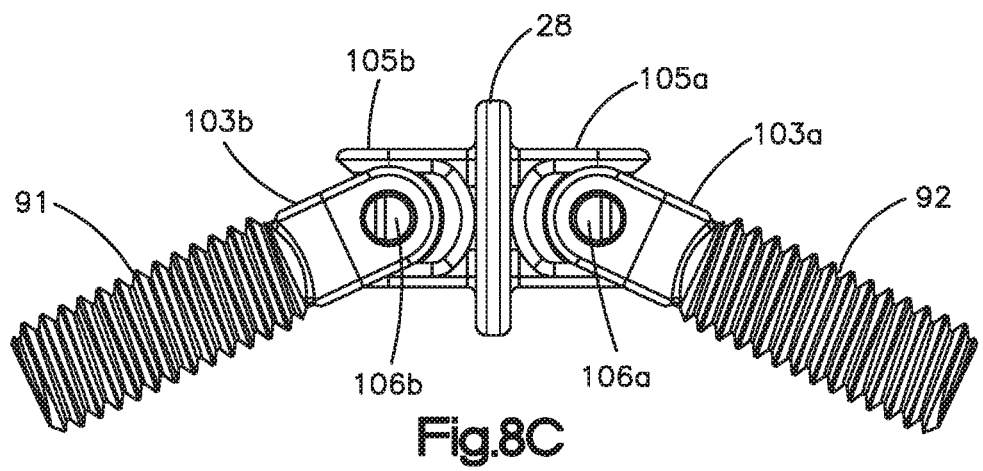
FIG. 8C is a top view of the actuation member shown in FIG. 8A.
Figure 8D:
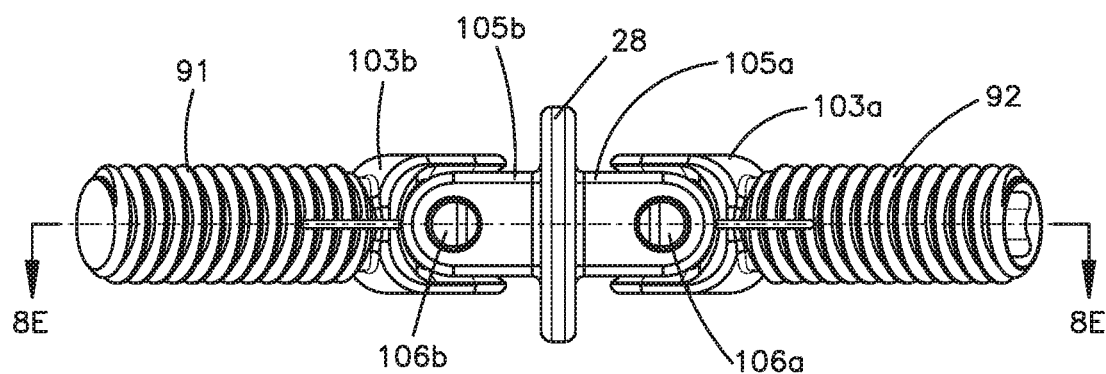
FIG. 8D is a side view of the actuation member shown in FIG. 8A.
Figure 8E:
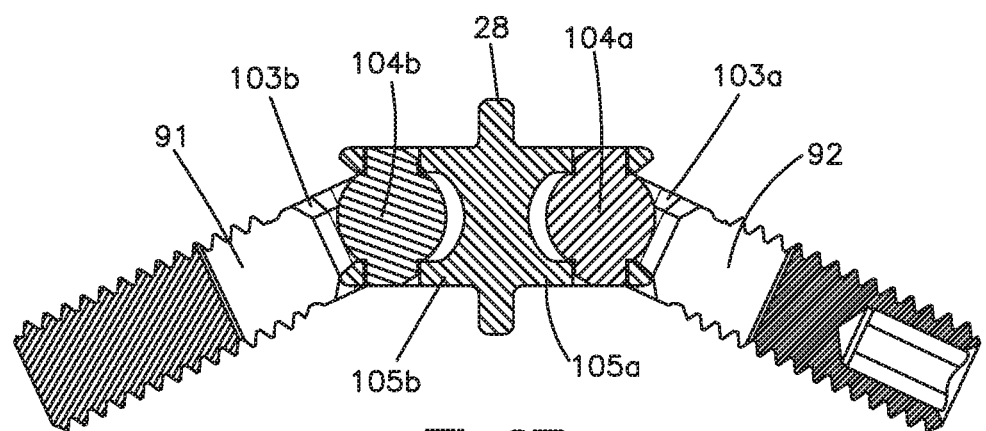
FIG. 8E is a sectional view of the actuation member shown in FIG. 8D.
Figure 9C:
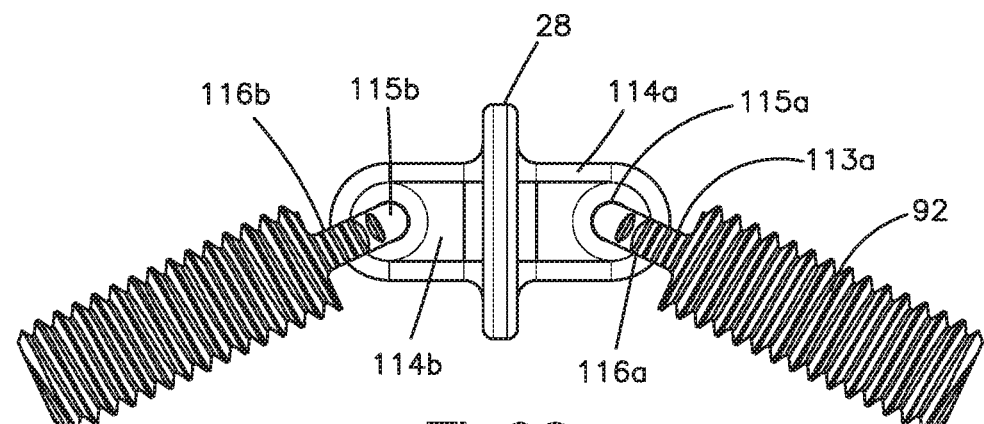
FIG. 9C is a top view of the actuation member shown in FIG. 9A.
Figure 9D:
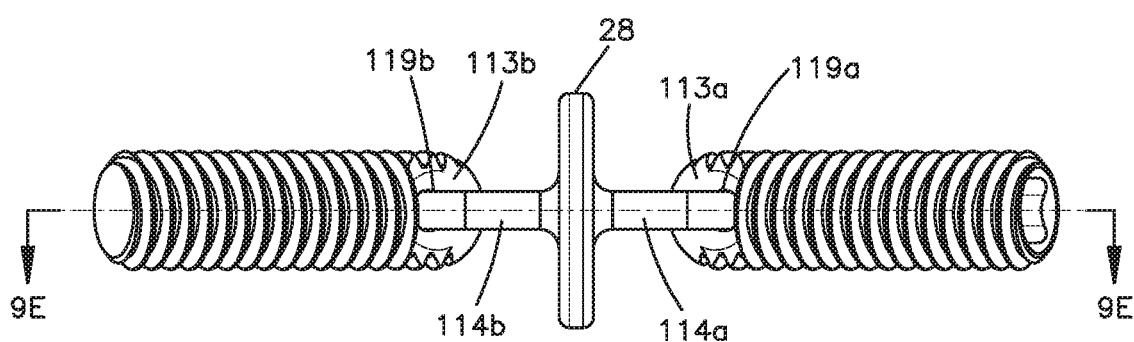
FIG. 9D is a side view of the actuation member shown in FIG. 9A.
Figure 9E:
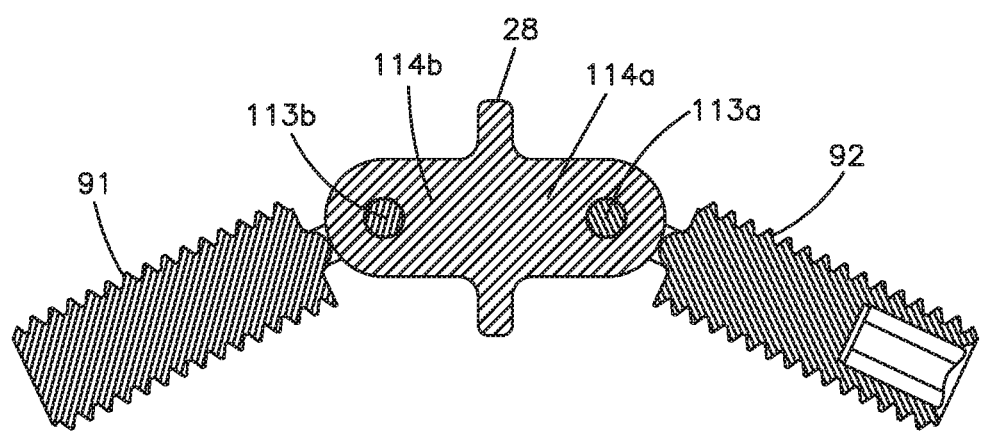
FIG. 9E is a sectional view of the actuation member shown in FIG. 9D.
Figure 10C:
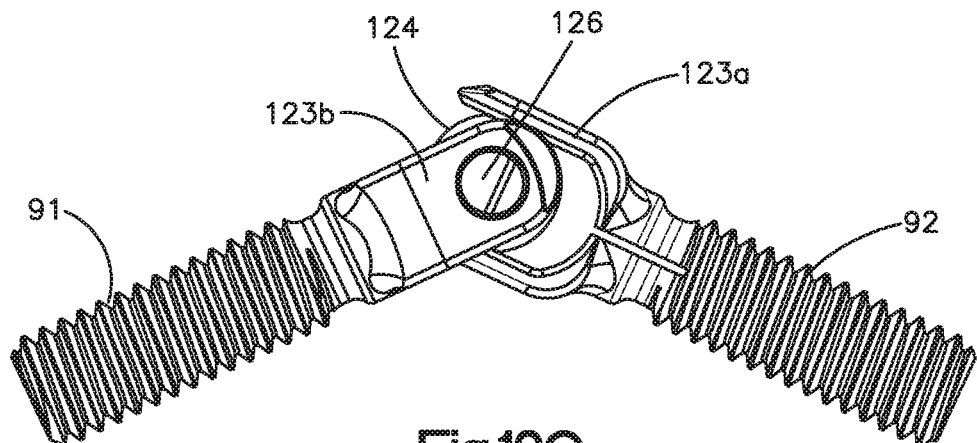
FIG. 10C is a top view of the actuation member shown in FIG. 10A.
Figure 10D:
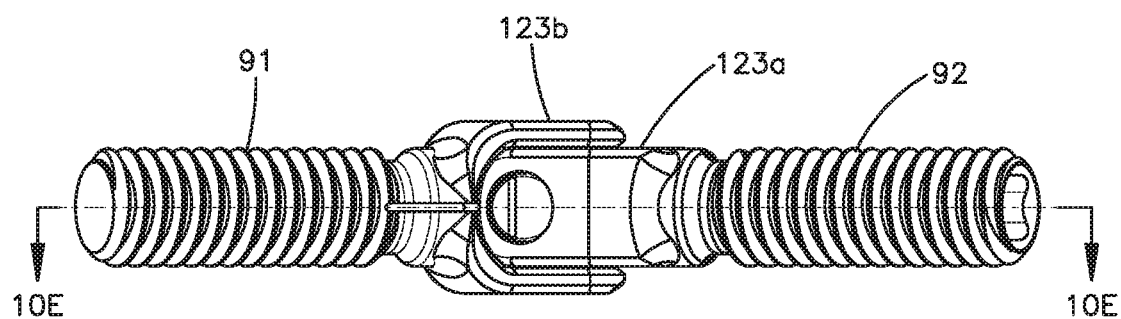
FIG. 10D is a side view of the actuation member shown in FIG. 10A.
Figure 10E:
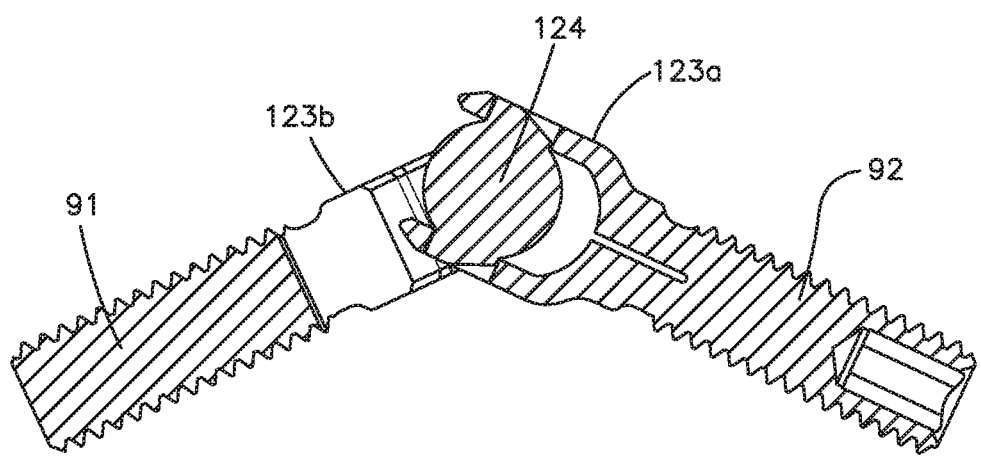
FIG. 10E is a sectional view of the actuation member shown in FIG. 10D.
Figure 11A:
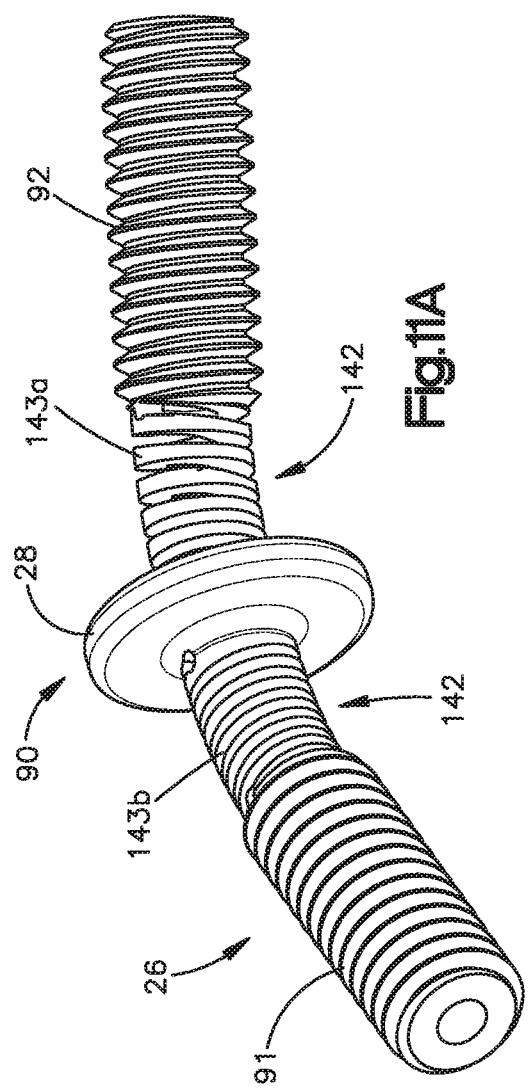
FIG. 11A is a perspective view of another embodiment for the actuation member of the implant shown in FIG. 1.
Figure 11B:
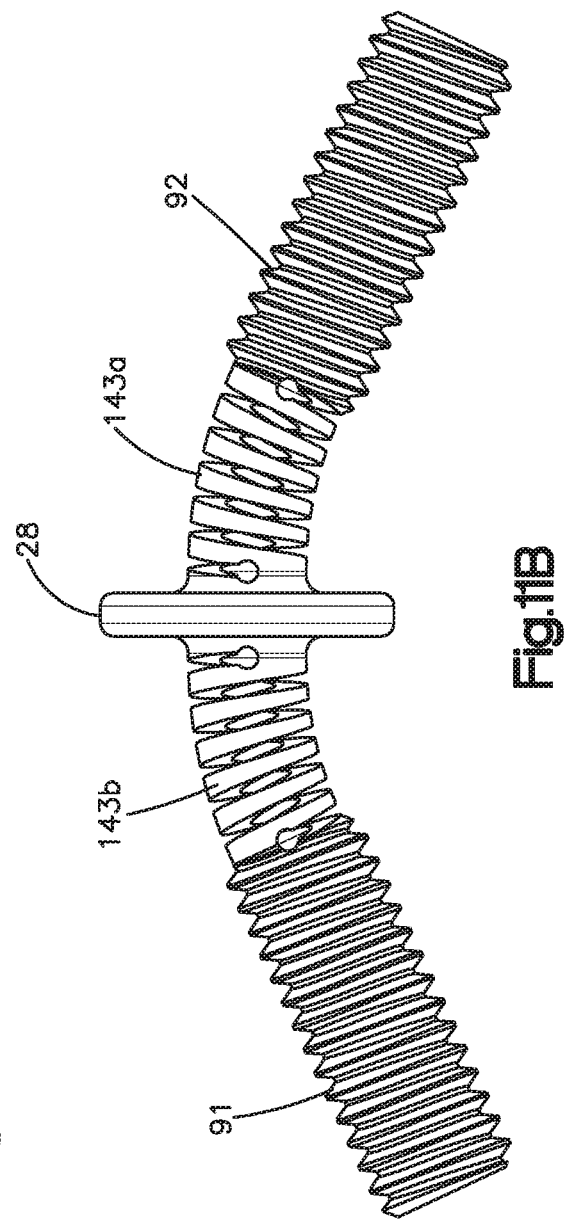
FIG. 11B is a top view of the actuation member shown in FIG. 11A.

Referring to FIGS. 3-4D, the inferior endplate 20 is configured for coupling with the first wedge member 22, the second wedge member 24, and at least a portion of the flange 28. The inferior endplate 20 can define a cavity 42 configured to partially house the first and second wedge members 22 and 24, and the actuation member 26. The inferior endplate 20 has an inferior inner surface 133 that includes a preferably planar surface 35a that forms the top surface of the two lateral side walls 36i and 40i that can be preferably designed to match up to similarly angled opposing surfaces on the superior endplate 18, and a multi-contoured surface 35b that forms part of the channel 135. The inferior endplate 20 also defines first and second ramp surfaces 44 and 46. The inferior endplate 20 further defines a first side surface 33a and a second side surface 33b opposite the first side surface 33a. The first and second side surfaces 33a and 33b extend between the bone-contacting surface 132 and the top planar surface 35a along the transverse direction T. The inferior endplate 20 thus defines a first sidewall 36i and a second sidewall 40i spaced from the first sidewall 36i along the lateral direction A. As illustrated, the channel 135 extends along the length of the inferior endplate 20 and along the lateral direction A between the opposed first and second sidewalls 36i and 40i. In the embodiment shown, the first and second sidewalls 36i and 40i converge with the inferior bone contacting surface 132 to form a tapered insertion end 16 (FIG. 2A).

Continuing with FIGS. 3-4D, the first and second sidewalls 36i and 40i are configured to receive the flange 28. The first sidewall 36i can define at least one slot, for instance a first slot 52 for receiving a portion of the flange 28 located on the actuation member 26. The first slot 52 is disposed in sidewall 40i at a location between the insertion end 12 and the trailing end 14 of the inferior endplate 20. The sidewall 36i can define at least one or second slot 54 for receiving another portion of the flange 28. The second slot 54 is disposed in the sidewall 36i at a location between the insertion end 12 and the trailing end 14. The second slot 54 is aligned, for instance laterally aligned, with and opposing the first slot 52 such that each slot 52 and 54 is positioned to receive a portion of the flange 28. The slots 52 and 54 are also configured to mate with the structure of the flange 28. For instance, the slots 52, 54 have an inner profile that is curvilinear and corresponds to the curvilinear profile of the flange 28. In other alternate embodiments, the slots 52 and 54 may have a rectilinear shape. It should be appreciated that the slots 52 and 54 may have any desired shape that can slidingly receive a portion of the flange 28. For example, if the flange 28 has a square profile, the slots 52 and 54 can be configured to mate with the square shaped flange. In alternate embodiments, the walls 36$i$ and 40$i$ can include a plurality of spaced slots spaced apart along the length of the implant 10 and disposed on the sidewalls 36$i$ and 40$i$ to receive a corresponding number of flanges or flanges portions extending from the actuation member 26.

The inner surface 133 of the inferior endplate 20 is also designed with a feature to couple the wedge members 22, 24 with the endplate. In one embodiment, along inner walls 39$i$, 45$i$ of the sidewall 36$i$ and 40$i$, respectively, there is a groove 37$i$ cut into the inner walls 39$i$, 45$i$ in the lateral direction A. The grooves 37$i$ are configured to engage a corresponding tab portion of the first and second wedge members 22 and 24 as further detailed below. The inferior endplate 20 has four grooves 37$i$ that are in two sets of pairs. The grooves 37$i$ extend in a parallel fashion to the ramp surfaces 44, 46 along the length of the implant 10. The pair of grooves 37$i$ on the first side 3 of the inferior endplate 20 extend from a point adjacent the trailing end 14 toward the middle section 7 of the implant 10 and parallel ramp surface 46 in a direction toward the inferior surface 132 in the transverse direction T. In a similar fashion, on the opposite second side 5 of the implant, the pair of grooves 37$i$ extend from a point adjacent the insertion end 12 toward the middle section 7 of the implant 10 and parallel ramp surface 44 in a direction toward the inferior surface 132 in the transverse direction T. The grooves 37$i$ extend toward the middle section 7 and terminate at a point either at the longitudinal center, or near the longitudinal center of the implant 10 or if a flange 28 is present, preferably before the slots 52, 54. While each side 3, 5 is illustrated has having a pair of grooves 37$i$, each side 3, 5 can have a single groove, or more than two grooves or other form of recess to capture the wedge members 22, 24.

Continuing with FIGS. 3-4D, the inferior endplate 20 defines ramp surfaces 44 and 46, for instance a first ramp surface 44 and a second ramp surface 46 that are configured to mate with and slide along portions of the first and second wedge members 22 and 24. The first ramp surface 44 extends from a point proximate the insertion end 12 toward the middle section 7 on an angle toward the inferior bone contacting surface 132. The ramp surface 44 is declined to abut and slidingly receive a portion of the second wedge member 24. The second ramp surface 46 extends from a point proximate the trailing end 14 toward the middle section 7 on an angle toward the inferior bone contacting surface 132, and is declined to abut and slidingly receive a portion of the first wedge member 22. The ramps surfaces 44 and 46 also extend laterally along the lateral direction A between the opposing first and second walls 36$i$ and 40$i$. Each ramp surface 44 and 46 can define a ramp angle β (not shown) defined with respect to planar surface 35$a$. It should be appreciated that the angle β can vary as needed, and preferably is between about 10° and about 65°. The inferior endplate 20 can also define a curvilinear portion 48 disposed at the trailing end 14 that is cut into the second ramp surface 46. The curvilinear portion 48 is configured to align with a corresponding curvilinear portion on the superior endplate 18. When the endplates 18 and 20 are in the collapsed configuration as shown in FIG. 2A, the curvilinear portions define an access opening 50 that provides access to the actuation member 26, as further detailed below.

As shown in FIGS. 4E-4H, the superior endplate 18 is configured similarly to the inferior endplate 20. The superior endplate 18 thus includes similar structural features that correspond to the structural features described above with respect to the inferior endplate 20. The two endplates are designed to close against each other and house the actuation member 26 with the wedge members 22, 24 connected thereto. The superior endplate 18 is configured for coupling with the first wedge member 22, the second wedge member 24, and at least a portion of the flange 28. The superior endplate 18 can define a cavity 42 configured to partially house the first and second wedge members 22 and 24, and the actuation member 26. The superior endplate 18 has a superior inner surface 33 that includes a preferably planar surface 35$a$ that forms the top surface of the two lateral side walls 36$s$ and 40$s$ that can be preferably designed to match up to similarly angled opposing surfaces on the inferior endplate 20, and a multi-contoured surface 35$b$ that forms part of the channel 135. The superior endplate 18 also defines first and second ramp surfaces 44 and 46. The superior endplate 18 further defines a first side surface 33$a$ and a second side surface 33$b$ opposite the first side surface 33$a$. The first and second side surfaces 33$a$ and 33$b$ extend between the bone-contacting surface 32 and the top planar surface 35$a$ along the transverse direction T. The superior endplate 18 thus defines a first sidewall 36$s$ and a second sidewall 40$s$ spaced from the first sidewall 36$s$ along the lateral direction A. As illustrated, the channel 135 extends along the length of the superior endplate 18 and along the lateral direction A between the opposed first and second sidewalls 36$s$ and 40$s$. In the embodiment shown, the first and second sidewalls 36$s$ and 40$s$ converge with the superior bone contacting surface 32 to form a tapered insertion end 16 (FIG. 2A).

Continuing with FIGS. 4E-H, the first and second sidewalls 36$s$ and 40$s$ are configured to receive the flange 28. The first sidewall 36$s$ can define at least one slot, for instance a first slot 52 for receiving a portion of the flange 28 located on the actuation member 26. The first slot 52 is disposed in sidewall 40$s$ at a location between the insertion end 12 and the trailing end 14 of the superior endplate 18. The sidewall 36$s$ can define at least one or second slot 54 for receiving another portion of the flange 28. The second slot 54 is disposed in the sidewall 36$s$ at a location between the insertion end 12 and the trailing end 14. The slot 54 is aligned, for instance laterally aligned, with and opposing the slot 52 such that each slot 52 and 54 is positioned to receive a portion of the flange 28. The slots 52 and 54 are also configured to mate with the structure of the flange 28. For instance, the slots 52, 54 have an inner profile that is curvilinear and corresponds to the curvilinear profile of the flange 28. In other alternate embodiments, the slots 52 and 54 may have a rectilinear shape. It should be appreciated that the slots 52 and 54 may have any desired shape that can slidingly receive a portion of the flange 28. For example, if the flange 28 has a square profile, the slots 52 and 54 can be configured to mate with the square shaped flange. In alternate embodiments, the walls 36$s$ and 40$s$ can include a plurality of spaced slots spaced apart along the length of the implant 10 and disposed on the sidewalls 36$s$ and 40$s$ to receive a corresponding number of flanges or flanges portions extending from the actuation member 26.

The inner surface 33 of the superior endplate 18 is also designed with a feature to couple the wedge members 22, 24 with the endplate. In one embodiment, along inner walls 39s, 45s of the sidewall 36s and 40s, respectively, there is a groove 37s cut into the inner walls 39s, 45s in the lateral direction A. The grooves 37s are configured to engage a corresponding tab portion of the first and second wedge members 22 and 24 as further detailed below. The superior endplate 18 has four grooves 37s that are in two sets of pairs. The grooves 37s extend in a parallel fashion to the ramp surfaces 44, 46 along the length of the implant 10. The pair of grooves 37s on the first side 3 of the superior endplate 18 extend from a point adjacent the trailing end 14 toward the middle section 7 of the implant 10 and parallel ramp surface 46 in a direction toward the superior surface 32 in the transverse direction T. In a similar fashion, on the opposite second side 5 of the implant, the pair of grooves 37s extend from a point adjacent the insertion end 12 toward the middle section 7 of the implant 10 and parallel ramp surface 44 in a direction toward the superior surface 32 in the transverse direction T. The grooves 37s extend toward the middle section 7 and terminate at a point near the longitudinal center of the implant 10, and if the flange 28 is present in the design then preferably before the slots 52, 54. While each side 3, 5 is illustrated has having a pair of grooves 37s, each side 3, 5 can have a single groove, or more than two grooves or other form of recess to capture the wedge members 22, 24.

Continuing with FIGS. 4E-H, the superior endplate 18 defines ramp surfaces 44 and 46, for instance a first ramp surface 44 and a second ramp surface 46 that are configured to mate with and slide along portions of the first and second wedge members 22 and 24. The first ramp surface 44 extends from a point proximate the insertion end 12 toward the middle section 7 on an angle toward the superior bone contacting surface 32. The first ramp surface 44 is inclined to abut and slidingly receive a portion of the second wedge member 24. The second ramp surface 46 extends from a point proximate the trailing end 14 toward the middle section 7 on an angle toward the superior bone contacting surface 32, and is inclined to abut and slidingly receive a portion of the first wedge member 22. The ramp surfaces 44 and 46 also extend laterally along the lateral direction A between the opposing first and second walls 36s and 40s. Each ramp surface 44 and 46 can define a ramp angle β (not shown) defined with respect to planar surface 35a. It should be appreciated that the angle β can vary as needed, and preferably is between about 10° and about 65°. The superior endplate 18 can also define a curvilinear portion 48 disposed at the trailing end 14 that is cut into the second ramp surface 46. The curvilinear portion 48 is configured align with a corresponding curvilinear portion on the inferior endplate 20. When the endplates 18 and 20 are in the collapsed configuration as shown in FIG. 2A, the curvilinear portions define an access opening 50 that provides access to the actuation member 26, as further detailed below.

The superior and inferior endplates 18, 20 are designed to be mated together. In a preferred embodiment, the two endplates are mated together by the wedge members 22, 24 that track within the grooves 37. The planar surfaces 35a of the superior and inferior endplates 18, 20 are designed to contact, or come close to contact, with each other when the implant is in its collapsed position (FIG. 2A). The superior endplate 18 and inferior endplate 20 can define opposing indentations 98 at the trailing end 14 of the implant 10. The indentations 98 are configured to receive a portion of an insertion tool (not shown).

The superior endplate 18 and inferior endplate 20 can also define respective openings or through-holes 30. Each opening or through-hole 30 has been configured to receive at least a portion of the first and second wedge members 22 and 24 to maximize the compact design and the expansion characteristics of the implant 10. The openings 30 partially receive portions of the first and second wedge members 22 and 24 when the implant 10 is in the collapsed configuration C (FIG. 2A), which allows for the dimensions of the first and second wedge members 22 and 24 to be increased over wedge members used in implants without an opening 30 configured to permit a portion of the wedge member to extend therethrough. Thus, the implant 10 has a collapsed configuration that is compact and less invasive, and an expanded configuration that is dimensionally stable. The openings 30 have the additional benefit of promoting bone growth when implanted in the intervertebral space 9. The opening 30 extends through the superior endplate 18 and similarly through the inferior endplate.

Referring to FIGS. 3 and 5A-5D, the first wedge member 22 and the second wedge member 24 are configured for slidable coupling to the superior and inferior endplates 18 and 20. The first and second wedge members 22 and 24 are configured similarly, and for illustrative purposes, only the first wedge member 22 will be described below. The first wedge member 22 defines a wedge body 74 extending along a central wedge axis CL between a narrow, outer end 75 and a wider, inner end 76 spaced from the outer end 75 along the central wedge axis CL. The wedge axis CL is preferably aligned with the central axis of the actuation member 26 and extends along the length of the wedge (in the embodiment shown, the implant 10 is designed to expand evenly in the superior and inferior directions because the wedges are designed in a symmetric fashion; the wedge could be designed with different angles for the wedge faces (and even one side could be designed with a flat face) so that expansion can be uneven in the superior and inferior directions). As show in FIGS. 3 and 7B, the first wedge narrow end 75 is positioned facing toward the outer or trailing end 14 of the implant 10, while the inner wide end 76 is positioned to face the middle portion 7 (and opening 30) of the implant 10. Further, the second wedge member 24 has a wedge body wherein the narrow outer end 75 is positioned facing toward the distal or insertion end 12 of the implant 10 and the inner wide end 76 is positioned facing toward the middle portion 7 (and opening 30) of the implant.

The wedge body 74 rides along and on the actuation member 26 to provide a mechanical means to separate the superior and inferior endplates 18, 20 to expand the implant 10. The wedge body 74 has a superior surface 77 and an opposing inferior surface 78. The superior surface 77 is angled from the narrow end 75 to the wide end 76, and the inferior surface 78 is similarly angled in the opposite direction. That angle is preferably between about 10° and about 65° with respect to the central axis CL for the superior surface 77 (and oppositely angled for the opposing surface 78). The angle preferably matches the angle for ramp surfaces 44, 46 and also the angle for the grooves 37. The wedge body 74 has protrusions, tabs, or tongues 82 extending along the sides 79, 80; the protrusions 82 are designed to fit and track within the grooves 37 such that as the wedge body 74 tracks along the actuation member 26 and the wedge members 22, 24 translate along the actuation member 26 away from the middle portion 7 the wedge members 22, 24 force the superior and inferior endplates 18, 20 away from each other relatively to cause the implant 10 to move from its collapsed position to its expanded position. The wedge body 74 has a superior edge 76s and an inferior edge 76i that define a height H1 for the wedge. The wedge body 74 has a central bore 81 that is preferably internally threaded to mate with the external threading on the actuation member 26.

Referring now to FIGS. 6A-6F, an embodiment for the actuation member 26 is depicted for description purposes. The actuation member 26 is configured to couple the first and second wedge members 22 and 24 together while also providing stability to the superior endplate 18 and inferior endplate 20 during implant expansion. The actuation member 26 is angled or curved at its middle section 90 that separates a second threaded section 91 and a first threaded section 92, the threaded sections 91, 92 having threads 99. The second threaded section 91 preferably is constructed such that there is a length of threaded straight rod having a center longitudinal axis CL1, and similarly the first threaded section 92 preferably is constructed such that there is a length of threaded straight rod having a center longitudinal axis CL2 (see FIG. 6E). The two center longitudinal axis lines CL1 and CL2 form an angle, $\alpha$, between them where the angle $\alpha$ is preferably between about 15° and about 75°; more preferably between about 15° and about 55°; more preferably between about 20° and about 50°; more preferably between about 25° and about 45°; more preferably between 30° and 40°, and in some embodiments between 33° and 37°. It is preferred that the first and second threaded sections 91, 92 each extend along a respective straight longitudinal section of the actuation member; however, the first and second threaded sections 91, 92 could be non-straight. In this latter configuration, a line can be drawn between a point in the center of the actuation member 26 at the beginning and at the end of the threads 99 on each of the first and second threaded sections 91, 92. The angle between these two lines would then form angle $\alpha$. The first and second threaded sections 91, 92 are preferably formed from steel, a titanium alloy, cobalt chrome, nitinol, polymers, or combinations of the foregoing materials.

In the embodiment depicted, the middle section 90 of the actuation member 26 can be constructed to include a flexible rod, which in this instance is in the form of a cable 93 that is made up of several wire segments 94. The middle section 90 is thus flexible and can enable the actuation member 26 to be rotated at one end by an actuation tool and that rotation will be maintained evenly for both the first and section threaded sections 91, 92. The pitch for the threads 99 on the first threaded section 92 is preferably the same as the pitch on the threads 99 on the second threaded section 91, except that the pitch is opposite hand between the first and second threaded section 91, 92. In this regard, the internal threads within the bores 81 for the first and second wedge members 22, 24 are designed to mate with the respective threads of the respective first and second threaded sections 91, 92, and are thus also opposite handed such that when the actuation member 26 rotates, the first and second wedge members 22 and 24 translate along the actuation member 26 toward each other or away from each depending on the rotation direction of the actuation member 26. The thread pattern on each threaded section 91, 92 may have the same pitch such that the first and second wedge members 22 and 24 can translate along the actuation member 26 at the same rate. The thread pitch can be different if needed when different distraction profiles are desired in the expanded configuration (e.g. kyphotic or lordotic). The proximal end 26p of the actuation member 26 can define a socket 26e configured to receive or support a portion of an insertion instrument, as further detailed below. The socket 26e can have any configuration as need to receive an instrument, such as hex, Phillips, flat, star, square, etc.

Thus, the shaft 95 of the actuation member 26 is curved along its length and defines a second threaded section 91 disposed distally relative to the flange 28 (or in the second side 5 proximate the insertion end 12), and a first threaded section 92 disposed proximally from the flange 28 (or in the first side 3 proximate the trailing end 14). The shaft 95 can have a length L1 extending from a distal end 96 along a central axis CA extending along the center of the shaft (see FIG. 6A) to a proximal end 97, where the length L1 can extend between about 24 to about 32 mm. The length of each of the first and second threaded sections 91, 92 is preferably equal, but can be different, and is preferably between about 6 mm to about 12 mm, more preferably between about 8 mm to about 9 mm. The length of middle section 90, which extends between the first and second threaded sections 91, 92 is preferably between about 8 mm to about 13 mm, more preferably between about 9 mm to about 11 mm. As shown in FIGS. 6A-E, the middle section 90 is constructed with a first cable section 93a extending between the second threaded section 91 and the flange 28 and a second cable section 93b extending between the first threaded section 92 and the flange 28. The length of each of the first and second cable sections 93a, 93b is preferably about equal, but can be different, and preferably is each from about 4 mm to about 7 mm long, and more preferably from about 4.5 mm to about 5.5 mm long along the central axis CA (see FIG. 6A). The flange 28 is preferably about 2 mm to about 5 mm long along the central axis CA between faces 28a, 28b, and preferably about 2 mm to about 3 mm in height between faces 28c, 28d (see FIG. 6E).

As seen in FIGS. 2A-2B and 7A-7D, the implant 10 can have initial dimensions and expanded dimensions. For instance, the implant can have first implant height D1 defined between the opposing first and second bone contacting surfaces 32 and 132 when the implant is in its collapsed position C, and second implant height D2 defined between the opposing first and second bone contacting surfaces 32 and 132 when the implant is in its expanded position E. The distance is measured from the surfaces 32, 132, and not from the tops of any textures 41 (teeth, etc.) that are commonly used with such surfaces. In an embodiment, the first implant height D1 can range between about 7 mm and 15 mm, preferably between about 7 mm and 10 mm, and the second expanded implant height D2 can range between about 10 mm and 20 mm, preferably between about 10 mm and 13 mm. In the expanded position E, the opposed superior and inferior inner planar surfaces 35a, which in the collapsed position C preferably abut one another, can be spaced apart any distance as desired within the stated range, such as between about 3 mm and 5 mm. For instance, in one embodiment, the first height D1 can be 7 mm while the expanded, second height D2 can be 10 mm. In another embodiment, the first height D1 can be 9 mm and the expanded, second height D2 can be 13 mm. Other dimensions are possible as well. For example first heights can be up to 7 mm, 9 mm, or greater. The implant 10 also has a width, and in one embodiment, the first and second bone contacting surfaces 32 and 132 can define a dimension in the lateral direction A as desired, such as between 8 mm and 12 mm.

The overall system includes one or more insertions tools. An insertion tool can include a handle and a shaft extending from the handle toward an implant supporting end. The implant supporting end can be configured to support, for instance carry or engage with a portion of the implant 10. The implant supporting end can include spaced apart tabs configured and sized to be received in the implant indentations 98. When the implant tabs engage the indentations 98, the tool can position and/or insert the implant 10 into the intervertebral space 9. An additional tool can be used to expand the implant 10 from the collapsed configuration C to the expanded configuration E. This tool can include a handle and a shaft extending from the handle toward a working end configured to engage the proximal end 26p of the actuation member 26, such that rotation of the tool can cause rotation of the actuation member 26.

Referring to FIGS. 7A-7D, implant 10 is configured to expand from the collapsed configuration C (FIG. 7B) to the expanded configuration E (FIG. 7D). When in the first or collapsed configuration C, the first and second wedge members 22 and 24 are disposed in the implant such that the inner ends 76 face and are spaced apart from each other to define a gap therebetween extending over the middle section 90. The first and second wedge members 22, 24 are threaded onto the actuation member 26 such that the first threaded section 92 is disposed within the bore 81 of the first wedge member 22 and the second threaded portion 91 is disposed within the bore 81 of the second wedge member 24. In the collapsed position C, the wedge members 22, 24 are preferably located near or at the inner ends 61 of the threaded sections 91, 92, and are spaced apart from the sides 28a, 28b of the flange. The inclined surfaces 77 and 78 of the wedge members 22, 24 are adjacent to opposing ramp surfaces 44 and 46 of the respective inferior and superior endplates 20, 18. In one embodiment, the inner end superior edge and inferior edges 76s and 76i extend into the opening 30 and can be located within or above/below a plane containing the bone contacting surfaces 32, 132. Portions of the first and second wedge members 22 and 24, for instance edges 76s, 76i, disposed in the opening 30 allows for a wedge profile that aids the endplates 18 and 20 separation with relatively little advancement of the first and second wedge members 22 and 24 along the actuation member 26.

When the actuation member 26 is rotated via a tool engaged at the proximal end 26p, the first threaded portion 92 of the actuation member 26 causes the first wedge member 22 to translate toward the trailing end 14 of the implant 10. The inclined surfaces 77 and 78 bear against the ramp surfaces 44 and 46 to separate the superior endplate 18 from the inferior endplate 20 along the transverse direction to move the implant 10 from the collapsed position C to the expanded position E. The protrusions or tabs 82 of the first wedge member 22 slide along the grooves 37i, 37s in a controlled manner. In conjunction, because the middle portion 90 of the actuation member 26 is a flexible cable, at the same time while the first wedge member 22 is translating toward the implant trailing end 14, the second threaded portion 91 of the actuation member 26 engages the bore 81 of the second wedge member 24 and causes the second wedge member 24 to translate toward the insertion end 12 of the implant 10. Again, the inclined surfaces 77 and 78 of the second wedge member 24 slide along the ramp surfaces 44 and 46 so as to separate the superior endplate 18 from the inferior endplate 20 along the transverse direction T. Again, the protrusions or tabs 82 of the second wedge member 24 slide along respective grooves 37s, 37i. The flange 28 remains disposed in the slots 52, 54 during actuation of the implant 10 and provides additional stability against sheer when the implant 10 is expanded. The embodiment shown in FIGS. 7A-7D illustrates the superior endplate 18 separating from the inferior endplate 20 along a transverse direction T while remaining generally parallel to each other. In other alternate embodiments, the implant can be configured to such that a lordotic or kyphotic distraction is achieved. For example, the threaded portions of the actuation member can be configured to cause one wedge member to translate at a faster rate compared to the other wedge member. In such an embodiment, when the implant 10 is expanded, the superior endplate 18 will be angularly offset from the inferior endplate 20.

The implant 10 can be used in TLIF surgical procedures. In general terms, the intervertebral disc space 9 is prepared by removing the appropriate amount of natural disc material to the surgeon's preference and preparing the endplate vertebral surfaces 6, 8 for receiving the implant 10. The implant 10 is inserted into the intervertebral space 9 defined between a superior vertebral body 2 and an inferior vertebral body 4. Preferably, the intervertebral implant 10 is inserted into the intervertebral space 9 in the fully collapsed configuration, although the implant 10 could be slightly expanded. The method further includes the step of expanding the intervertebral implant 10 from a collapsed configuration to a final expanded configuration. When the implant 10 is in the collapsed configuration, the first and second bone contacting surfaces 32 and 132 are spaced from each other a first distance in the transverse direction T.

As described above, the actuation member 26 is rotatable about its central axis CA to cause the implant 10 to expand from a collapsed configuration to an expanded configuration. As described above, a tool is used to rotate the actuation member 26 to cause the first and second wedge members 22 and 24 translate along the actuation member 26 and to move away from each other to expand the implant 10. The actuation member 26 can be rotated until the first wedge member 22 abuts a stop member 63, which prevents further rotation of the actuation member 26 in the expansion direction. The stop member 63 can be a ring that has a threaded internal bore and that is placed onto the first threaded section 92 after the first wedge member 22 is assembled onto the implant 10. The actuation member 26 is rotatable in a contraction direction opposite the expansion direction so as to cause the wedge members 22 and 24 to move toward each other, thereby moving the endplates 18 and 20 toward each other in a direction from an expanded position toward a collapsed configuration. The implant 10 thus can be expanded in the cranial-caudal or superior-inferior direction, the transverse direction T, to engage the adjacent vertebral bodies 2, 4.

There are other mechanical components that can be used in the present invention to provide for the simultaneous rotation of the first and second threaded sections 91 and 92 of the actuation member 26 to cause the first and second wedge members 22, 24 to simultaneously expand the implant 10 by imparting a rotational force upon the actuation member 26 at its proximal end 26p. For example, in FIGS. 8A-8E, a dual universal joint embodiment is shown for the actuation member 26. The dual universal joint 102 is located in the middle section 90 of the actuation member 26. The dual universal joint 102 is constructed with a first universal joint assembly 107 and a second universal joint assembly 108. The first universal joint assembly 107 has a fork 103a coupled to the first threaded section 92, preferably integrally formed with the first threaded section 92. The fork 103a is coupled to a center block (or ball) 104a by way of pins 106a that extend through opposed openings 109a in the fork 103a. The center block 104a is also coupled to center fork 105a by way of pins 106a that extend through openings 109a. The second universal joint assembly 108 has a fork 103b coupled to the second threaded section 91, preferably integrally formed with the second threaded section 91. The fork 103b is coupled to a center block 104b by way of pins 106b that extend through opposed openings 109b in the fork 103b. The center block 104b is also coupled to center fork 105b by way of pins 106b that extend through openings 109b. In this embodiment, the dual universal joint 102 along with the first and second threaded sections 92, 91 form the actuation member 26 for the implant 10. Apart from the mechanical mechanism for permitting the simultaneous rotation of the two threaded sections 91, 92 being different between this dual universal joint 102 embodiment and the flexible cable 93 embodiment in FIGS. 2-7, the remaining parts and function of the implant are the same. In that regard, when the actuation member 26 having the dual universal joint 102 is used in the implant the angle between the first threaded section 91 and the second threaded section 92 is the same as described above with the flexible cable 93 embodiment.

Another embodiment for the actuation member 26 is shown in FIGS. 9A-9E, a turn buckle embodiment. The turn buckle 112 is located in the middle section 90 of the actuation member 26. The turn buckle 112 is constructed with a first inner end 113a coupled to the first threaded section 92, preferably integrally formed with the first threaded section 92. The first inner end 113a is partially threaded with threads 99 but is cut along its two sides 116a to form a reduced profile loop section and the sides 116a have a hole 119a. An inner shaft 114a also has a loop section with a hole 115a. The hole 119a of the inner end 113a receives the loop section of the inner shaft 114a and the hole 115a of the inner shaft 114a receives the loop section of the inner end 113a to form part of the turn buckle 112 on the first threaded section 92 side of the actuation member 26. The turn buckle 112 is further constructed with a second inner end 113b coupled to the second threaded section 91, preferably integrally formed with the second threaded section 91. The second inner end 113b is partially threaded with threads 99 but is cut along its two sides 116b to form a reduced profile loop section and the sides 116b have a hole 119b. An inner shaft 114b also has a loop section with a hole 115b. The hole 119b of the inner end 113b receives the loop section of the inner shaft 114b and the hole 115b of the inner shaft 114b receives the loop section of the inner end 113b to form part of the turn buckle 112 on the second threaded section 91 side of the actuation member 26. In this embodiment, the turn buckle 112 along with the first and second threaded sections 92, 91 form the actuation member 26 for the implant 10. Apart from the mechanical mechanism for permitting the simultaneous rotation of the two threaded sections 91, 92 being different between this turn buckle 112 embodiment and the flexible cable 93 embodiment in FIGS. 2-7, the remaining parts and function of the implant are the same. In that regard, when the actuation member 26 having the turn buckle 112 is used in the implant the angle between the first threaded section 91 and the second threaded section 92 is the same as described above with the flexible cable 93 embodiment.

Still another embodiment for the actuation member 26 is shown in FIGS. 10A-10E, a universal joint embodiment. The universal joint 122 is located in the middle section 90 of the actuation member 26. The universal joint 122 is constructed with a fork 123a coupled to the first threaded section 92, preferably integrally formed with the first threaded section 92. The fork 123a is coupled to a center block (or ball) 124 by way of pins 126 that extend through opposed openings 129a in the fork 123a. The center block 124 is also coupled to opposing fork 123b by way of pins 126 that extend through openings 129b. The fork 123b coupled to the second threaded section 91, preferably integrally formed with the second threaded section 91. In this embodiment, the universal joint 122 along with the first and second threaded sections 92, 91 form the actuation member 26 for the implant 10. Apart from the mechanical mechanism for permitting the simultaneous rotation of the two threaded sections 91, 92 being different between this universal joint 122 embodiment and the flexible cable 93 embodiment in FIGS. 2-7, the remaining parts and function of the implant are the same, except that the flange 28 is not present in the embodiment as shown. In that regard, when the actuation member 26 having the universal joint 122 is used in the implant the angle between the first threaded section 91 and the second threaded section 92 is the same as described above with the flexible cable 93 embodiment.

Yet another drive mechanism that can form the basis for another embodiment for the actuation member 26 is shown in FIGS. 11A-11D, a dual wired cylinder embodiment. The dual wired cylinder 142 is also a flexible rod like the cable 93 embodiment and is located in the middle section 90 of the actuation member 26. The dual wired cylinder 142 is constructed with a first wired cylinder 143a coupled to the first threaded section 92, preferably integrally formed with the first threaded section 92. The first wired cylinder 143a is preferably formed from surgical grade metal alloy such as a titanium alloy as a wire turned to form a cylinder shape. At its opposite end, the first wired cylinder 143a is connected to a second wired cylinder 143b that is connected at its opposite end to the second threaded section 91. The flange 28 can optionally be formed between the first and second wired cylinders 143a, b as shown. In this embodiment, the dual wired cylinder 142 along with the first and second threaded sections 92, 91 form the actuation member 26 for the implant 10. Apart from the mechanical mechanism for permitting the simultaneous rotation of the two threaded sections 91, 92 being different between this dual wired cylinder 142 embodiment and the flexible cable 93 embodiment in FIGS. 2-7, the remaining parts and function of the implant are the same. In that regard, when the actuation member 26 having the dual wired cylinder 142 is used in the implant the angle between the first threaded section 91 and the second threaded section 92 is the same as described above with the flexible cable 93 embodiment.

Each of the superior endplate 18 and inferior endplate 20 can include one or more radiographic markers. The implant 10 can define one or more bores (not shown) sized and dimensioned to receive a radiographic marker therein. For example, a radiographic marker can be disposed near the nose 16 in either the superior endplate 18 or the inferior endplate 20, or both. The markers can thus identify the location of the nose 16 of the implant and also the extent of expansion of the implant 10 when the markers are located in each endplate. For example, when the implant 10 is inserted into the intervertebral space 9, and the implant 10 is expanded from the first configuration C to the expanded configuration E, the markers can separate along the transverse direction T. With image analysis, the extent of plate separation can be determined or indicated by observing the extent of separation between the markers disposed in the superior endplate 18 compared to the marker disposed in the inferior endplate 20.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An expandable implant for insertion into an intervertebral space between a superior vertebral body and an adjacent inferior vertebral body, the expandable implant comprising:
 a superior endplate having a superior outer surface configured to contact the superior vertebral body;
 an inferior endplate having an inferior outer surface configured to contact the inferior vertebral body;
 an actuation member disposed at least partially between the superior and inferior endplates, the actuation member having a first threaded section extending along a first central longitudinal axis of the actuation member and a second threaded section joined to the first threaded section and extending along a second central longitudinal axis of the actuation member, wherein the first central longitudinal axis and the second central longitudinal axis form an angle between about 15° and about 75°;
 a first wedge member threadedly mated with the first threaded section and a second wedge member threadedly mated with the second threaded section;
 wherein the actuation member is configured to be rotated about the first and second central longitudinal axes, thereby driving the first wedge member to translate along the first threaded section and the second wedge member to translate along the second threaded section, such that at least one of the inferior and superior endplates is urged to move away from the other of the inferior and superior endplates from a collapsed implant configuration to an expanded implant configuration, and
 wherein the actuation member comprises a dual universal joint located between the first threaded section and the second threaded section, the dual universal joint comprising a central narrow, circular flange.

2. The expandable implant of claim 1, wherein the actuation member comprises a distal end located proximate an insertion end portion of the expandable implant and proximate the second threaded section, and a proximal end located proximate the first threaded section, wherein the dual universal joint causes the second threaded section to rotate in a first rotational direction in response to the first threaded section being rotated in the first rotational direction.

3. The expandable implant of claim 2, wherein the central narrow, circular flange includes a distal flange fork component configured to operatively engage the second threaded section and a proximal flange fork component configured to operatively engage the first threaded section.

4. The expandable implant of claim 3, wherein the central narrow, circular flange has a height in a vertical direction greater than a height of the distal flange fork component and greater than a height of the proximal flange fork component.

5. The expandable implant of claim 3, wherein the distal flange fork component is connected to a distal center ball component, and the proximal flange fork component is connected to a proximal center ball component.

6. The expandable implant of claim 5, wherein the distal center ball component is connected to a distal actuation fork component connected to the second threaded section of the actuation member and the proximal center ball component is connected to a proximal actuation fork component connected to the first threaded section of the actuation member.

7. The expandable implant of claim 1, wherein the first threaded section is oppositely threaded from the second threaded section.

8. The expandable implant of claim 1, wherein the first wedge member has a superior inclined surface contacting a first superior ramp surface on an inner surface of the superior endplate.

9. The expandable implant of claim 8, wherein the first wedge member has an inferior inclined surface contacting a first inferior ramp surface on an inner surface of the inferior endplate.

10. The expandable implant of claim 1, wherein the first central longitudinal axis and the second central longitudinal axis form an angle between about 15° and about 55°.

11. The expandable implant of claim 1, wherein the first central longitudinal axis and the second central longitudinal axis form an angle between 30° and 40°.

12. An expandable implant for insertion into an intervertebral space between a superior vertebral body and an adjacent inferior vertebral body, the expandable implant comprising:
 a superior endplate having a superior outer surface configured to contact the superior vertebral body;
 an inferior endplate having an inferior outer surface configured to contact the inferior vertebral body;
 an actuation member disposed at least partially between the superior and inferior endplates, the actuation member having a first threaded section extending along a first central longitudinal axis of the actuation member and a second threaded section joined to the first threaded section by a middle section and extending along a second central longitudinal axis of the actuation member, wherein the first central longitudinal axis and the second central longitudinal axis form an angle between about 15° and about 75°, and wherein the first and second threaded sections are non-straight;
 a first wedge member threadedly mated with the first threaded section and a second wedge member threadedly mated with the second threaded section;
 wherein the actuation member is configured to be rotated about the first and second central longitudinal axes, thereby driving the first wedge member to translate along the first threaded section and the second wedge member to translate along the second threaded section, such that at least one of the inferior and superior endplates is urged to move away from the other of the inferior and superior endplates from a collapsed implant configuration to an expanded implant configuration.

13. The expandable implant of claim 12, wherein the first threaded section is oppositely threaded from the second threaded section.

14. The expandable implant of claim 12, wherein the first wedge member has a superior inclined surface contacting a first superior ramp surface on an inner surface of the superior endplate.

15. The expandable implant of claim 12, wherein the first wedge member has an inferior inclined surface contacting a first inferior ramp surface on an inner surface of the inferior endplate.

16. The expandable implant of claim 12, wherein the first central longitudinal axis and the second central longitudinal axis form an angle between about 15° and about 55°.

17. The expandable implant of claim 12, wherein the middle section is a flexible rod.

\* \* \* \* \*